(12) United States Patent
Herbst et al.

(10) Patent No.: US 9,731,100 B2
(45) Date of Patent: Aug. 15, 2017

(54) DEVICES AND METHODS FOR CONTROLLING DIETARY LIPID UPTAKE

(71) Applicant: Boston Scientific Scimed, Inc., Maple Grove, MN (US)

(72) Inventors: Thomas J. Herbst, Coon Rapids, MN (US); Arthur J. Foster, Blaine, MN (US); Lynne E. Swanson, Edina, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 218 days.

(21) Appl. No.: 14/658,434

(22) Filed: Mar. 16, 2015

(65) Prior Publication Data
US 2015/0265814 A1    Sep. 24, 2015

Related U.S. Application Data

(60) Provisional application No. 61/954,905, filed on Mar. 18, 2014.

(51) Int. Cl.
*A61M 27/00*    (2006.01)

(52) U.S. Cl.
CPC .................................. *A61M 27/002* (2013.01)

(58) Field of Classification Search
CPC ........ A61M 27/002; A61M 2202/0405; A61M 2230/005; A61F 2/04; A61B 5/418; F16K 37/0033; F16K 31/02
See application file for complete search history.

(56) References Cited

U.S. PATENT DOCUMENTS

| | | | |
|---|---|---|---|
| 5,391,143 A | 2/1995 | Kensey | |
| 5,830,172 A | 11/1998 | Leveen et al. | |
| 6,022,333 A * | 2/2000 | Kensey ............... | A61M 1/1678 604/29 |
| 6,190,347 B1 | 2/2001 | Kensey | |
| 8,322,365 B2 | 12/2012 | Wilson et al. | |
| 8,398,577 B2 | 3/2013 | Burnett | |
| 2005/0055009 A1 | 3/2005 | Rosenberg | |
| 2006/0074371 A1 | 4/2006 | McCusker et al. | |
| 2012/0029466 A1 | 2/2012 | Callaghan et al. | |
| 2014/0276344 A1 | 9/2014 | Herbst et al. | |

(Continued)

OTHER PUBLICATIONS

'Magnets and Electromagnets', Nov. 23, 1999.*

(Continued)

*Primary Examiner* — Tatyana Zalukaeva
*Assistant Examiner* — Benjamin Klein
(74) *Attorney, Agent, or Firm* — Bookoff McAndrews, PLLC

(57) ABSTRACT

Methods and devices for redirecting at least a portion of a fluid from the mesenteric lymphatic system for elimination from the body are disclosed. The fluid may be redirected for elimination through the urinary system, through the gastrointestinal system, or redirected outside the body. The device may include a valve to control a flow of the fluid. The methods and devices disclosed may prevent a portion of a patient's dietary lipids, including cholesterol, from being metabolized and absorbed, thereby reducing the total caloric load to assist in weight management and/or for prevention/treatment of atherosclerosis.

14 Claims, 13 Drawing Sheets

(56) References Cited

U.S. PATENT DOCUMENTS

| | | | | |
|---|---|---|---|---|
| 2015/0057596 A1* | 2/2015 | Lind | .................. | A61F 9/00781 604/9 |
| 2015/0257930 A1* | 9/2015 | Lind | .................. | A61F 9/00781 604/9 |
| 2015/0257931 A1* | 9/2015 | Sanchez | .............. | A61F 9/00781 604/9 |

OTHER PUBLICATIONS

Dixon, J. B, "Lymphatic Lipid Transport: Sewer or Subway?" *Trends Endocrinol. Metab.*, vol. 21, pp. 480-487 (2010).

Berg, J.M. et al., Biochemistry, 5th ed., Ch. 22, pp. 601-632 (2002).

Cheng, J-T. et al., "Chyluria Presenting as Milky Urine and Nephrotic-range Proteinuria," Int. Soc. Nephrol., vol. 70, pp. 1518-1522 (2006).

Mallick, A. et al., "Disorders of the Lymph Circulation: Their Relevance to Anaesthesia and Intensive Care," vol. 91, pp. 265-272 (2003).

Redgrave, T.G., "Chylomicrons in Disease-Future Challenges," *Atherosclerosis Supp.*, vol. 9, pp. 3-6 (2008).

Takechi, R. et al., "Chylomicron Amyloid-beta in the Aetiology of Alzheimer's Disease," *Atherosclerosis Supp.*, vol. 9, pp. 19-25 (2008).

Tomkin, G. H., "The Intestine as a Regulator of Cholesterol Homeostasis in Diabetes," *Atherosclerosis Supp.*, vol. 9, pp. 27-32 (2008).

\* cited by examiner

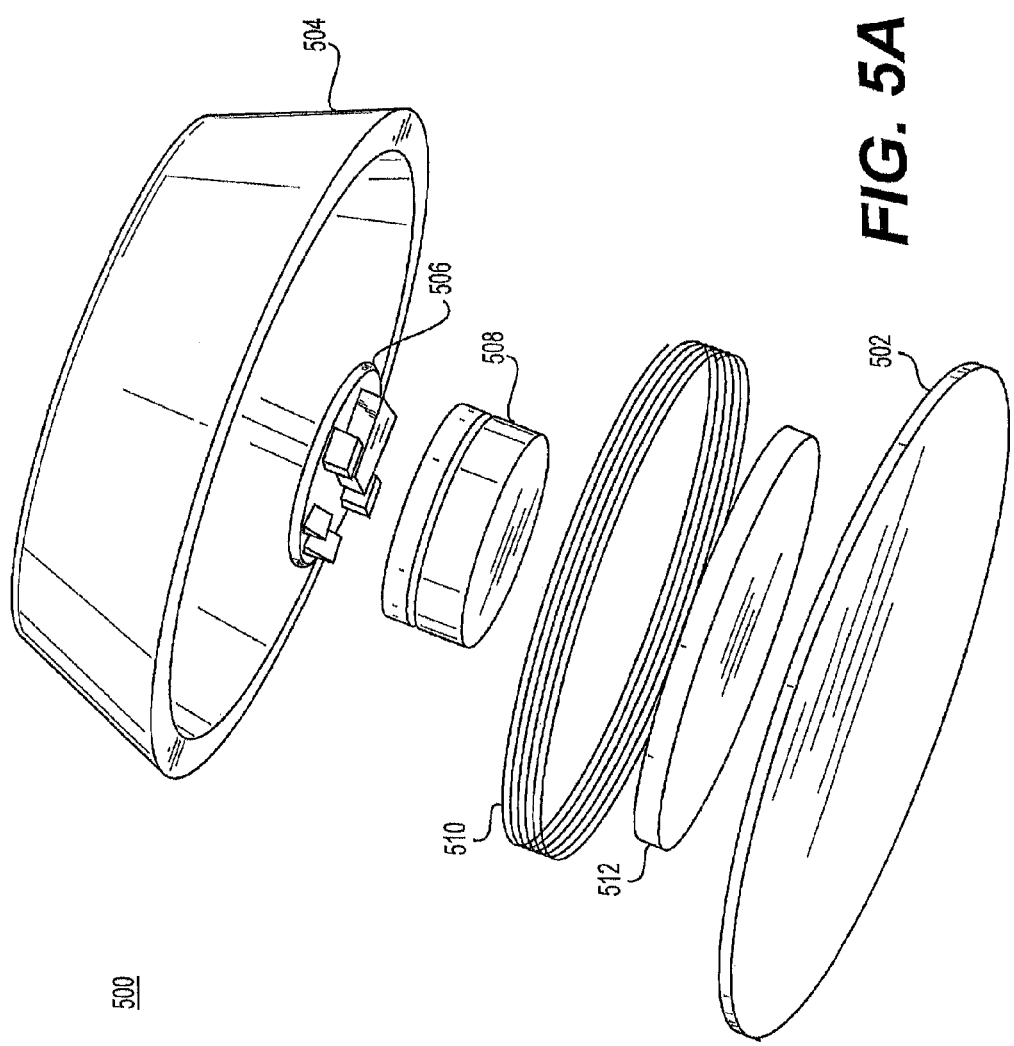

DEVICES AND METHODS FOR CONTROLLING DIETARY LIPID UPTAKE

CROSS-REFERENCE TO RELATED APPLICATIONS

This application claims the benefit of priority from U.S. Provisional Application No. 61/954,905, filed on Mar. 18, 2014, the entirety of which is incorporated herein by reference.

TECHNICAL FIELD

Various embodiments of the present disclosure relate generally to medical devices and related methods. More specifically, the present disclosure relates to devices and methods for controlling a flow of fluid from the lymphatic system, such as from the thoracic duct or cisterna chyli. Embodiments of the present disclosure may be useful in weight management, such as treatment of obesity, e.g., morbid obesity, and/or may be useful in the prevention and/or treatment of atherosclerosis.

BACKGROUND

Excess caloric intake can impair health. Weight management, for example, can be difficult for many people. Obesity is a condition where a person's body stores an excess amount of fat, and can be caused by ingesting an excess amount of calories via the alimentary tract system. The American Medical Association has officially recognized obesity as a disease that may require medical intervention for treatment and prevention. The amount and type of calories ingested can affect the risk of developing other health conditions, such as cardiovascular disease. Various treatments are available to treat obesity and the incidence of pathophysiology comorbidities. Those treatments include, for example, surgical procedures such as obstruction or bypass modalities of the digestive system, pharmaceutical drugs, and behavioral modification. Such treatments have at their core mechanism of action (MOA) a reduction in daily caloric load below physiologic basal maintenance needs, which for an adult male is about 2200 kcal/day (i.e., about 2200 food calories per day) and for an adult female about 1800 kcal/day (i.e., about 1800 food calories per day). MOAs leading to weight loss may include, for example, a reduction in calories ingested, decreased absorption, and/or hormonal changes that alter satiation (e.g., cause a person to feel full sooner).

There remains a need for alternative methods of achieving caloric load diminution to assist patients in improving their health, including weight management and vascular health.

SUMMARY OF THE DISCLOSURE

The present disclosure includes methods and devices for controlling a flow of fluid, e.g., from the lymphatic system, to redirect or shunt at least a portion of a patient's daily consumed calories at least temporarily to make them unavailable for intermediary metabolism and eliminate them from the body. The present disclosure further includes methods and devices for regulating and/or reducing the amount of lipids such as cholesterol and other lipid-containing components that are metabolized and absorbed in the body, e.g., for post-prandial control of hyperlipidemia/dyslipidemia.

The present disclosure includes medical devices useful in redirecting at least a portion of a fluid in a patient. The fluid may include fluid from the thoracic duct and/or cisterna chyli, such as chyle or any other fluid, including a fluid comprising lipids, cholesterol, and/or any other fatty acids or compounds generated following ingestion of food or drink, e.g., during digestion of the food or drink. In some aspects, the medical device may be configured to be implanted in a patient, such as for redirecting a fluid from a usual physiological pathway to an alternate pathway, such as a non-physiologic pathway, e.g., for shunting the fluid outside the patient's body, such as via the urinary system, via the gastrointestinal system, or via a stoma. The medical devices according to the present disclosure may be useful in controlling (e.g., regulating or limiting) or preventing caloric intake, controlling (e.g., regulating or limiting) or preventing lipid absorption, controlling weight management, treating obesity, controlling (e.g., regulating or limiting) or preventing metabolism and uptake of chylomicrons and other lipid-containing components in the body, and/or preventing atherosclerosis.

In at least one aspect, the medical device may comprise a housing. For example, the housing may have an inlet and an outlet, e.g., for passage of a fluid through the housing. In addition, the medical device may include a diaphragm. The diaphragm may be coupled to the housing. For example, the diaphragm may be enclosed within the housing or contained within the housing. In some aspects, the diaphragm may include a flexible material, although any biocompatible materials may be used. For example, the diaphragm may include one or more flexible materials such as silicone, polyurethane, or other flexible polymers or materials. Further, the diaphragm may include an aperture, e.g., an opening.

In some aspects, the medical device also may include a metallic element, which may be, for example, in the form of a circle. Other shapes also may be suitable, including but not limited to, oval, rectangular, square, or other polygonal shapes. The metallic element may be coupled to the diaphragm, such as attached, adhered to, or otherwise incorporated into the diaphragm such that the diaphragm and the metallic element may move as a unit. In some aspects, the metallic element also may include an aperture, e.g., an opening. Thus, in cases when the diaphragm and the metallic element are coupled together, the apertures of the diaphragm and the metallic element may be at least partially or entirely aligned to form or define a conduit, e.g., for passage of a fluid through the medical device. In some aspects, for example, the metallic element may be in the form of a metallic ring. The metallic element may comprise a ferrous material such as iron or an iron alloy, or may comprise a permanent magnet or other metal attracted to an electromagnet. In some aspects, the medical device may include more than one metallic element, such as a metallic ring and at least one other metallic element.

The medical device also may comprise a sealing element of any suitable shape, such as a ball. The sealing element may be at least partially or entirely aligned with the conduit defined by the diaphragm and the metallic element, or may be at least partially or entirely aligned with the aperture of the diaphragm and/or at least partially or entirely aligned with the aperture of the metallic element. Thus, the sealing element may selectively block passage of a fluid through the conduit, and/or through the aperture of the diaphragm or the aperture of the metallic element. For example, the diaphragm may be configured to move toward and away from the sealing element to control a rate of flow of a fluid through the medical device (e.g., through the conduit and/or aperture(s) of the diaphragm and/or metallic element). In some aspects, the medical device may include a valve seat disposed adjacent to the sealing element. For example, the valve seat may include an aperture at least partially aligned or completely aligned with the aperture of the diaphragm and/or the aperture of the metallic element, such that a conduit may be defined by the diaphragm, the metallic element, and the valve seat. The valve seat may comprise a metal or metal alloy such that the valve seat may comprise the metallic element, or one of two or more metallic elements of the medical device. For example, the valve seat may comprise a metal, e.g., a ferrous material such as iron or an iron alloy, or may comprise a permanent magnet or other metal attracted to an electromagnet. In some aspects, the medical device may comprise only one ferrous material (e.g., of a metallic ring or of a valve seat).

Thus, in some aspects, the medical device may include a housing, the housing including a diaphragm, at least one metallic element (which may include a valve seat), and a sealing element. The housing of the medical device may comprise an integral piece or may comprise an upper housing and a lower housing. For example, the upper housing may include an inlet and the lower housing may include an outlet. Other suitable forms of housings may be used according to the present disclosure. In some aspects, the sealing element may be coupled to a portion of the housing, such as the lower housing, via any suitable mechanism. For example, the sealing element may be attached to, adhered to, or otherwise incorporated into the lower housing. In some aspects, a position of the sealing element may be adjustable relative to the lower housing, e.g., to provide for multiple positions relative to the housing and/or to control an amount of pressure exerted on the valve seat, the metallic element, and/or the diaphragm. In some aspects, the medical device may include a one-way valve, e.g., to prevent flow of fluid in an undesired direction, such as from the outlet into the medical device. The medical device may be configured to inhibit or prevent deposition of material from a fluid flowing through the medical device, such as an interior surface comprising a polymer coating, e.g., a hydrophobic coating, and/or an interior surface functionalized with a polymer and/or active agent.

The medical device also may include an electromagnet. The electromagnet may include a coil and a power source. In some aspects, the electromagnet optionally also may include a core element, e.g., comprising a ferrous material, to increase the strength of the magnetic field generated by the electromagnet. Magnetic attraction between the electromagnet and a metal of a medical device (e.g., the at least one metallic element within the housing of the medical device or other metallic element of the medical device) may allow and prevent passage of a fluid through the medical device. In some aspects, for example, the strength of the magnetic attraction may selectively allow and prevent passage of the fluid, including control over a rate of passage of the fluid through the medical device, e.g., through a conduit and/or aperture(s) within the medical device. Thus, for example, increasing the strength of the magnetic field may increase a flow rate of the fluid through the housing, and decreasing the strength of the magnetic field may decrease the flow rate of the fluid through the housing.

In some aspects, the medical device also may include at least one integrated circuit. For example, the integrated circuit may be in communication with the electromagnet, e.g., configured to supply and terminate power to the electromagnet to generate and/or control a magnetic field. In some aspects, the integrated circuit may be in communication with at least one sensor. The sensor(s) may be implanted in the patient, may be coupled, attached, or integrated into the medical device, may be external to the patient, and/or may be coupled, attached, or integrated into a controller module inside or outside the patient. In some aspects, the sensor(s) may be configured to measure physiological information about the patient. For example, the integrated circuit may be configured to control the magnetic field based at least in part on the physiological information, such as information regarding a presence of a fluid, an absence of a fluid, a flow rate of a fluid, a pressure, and/or a temperature, among other possible physiological parameters. Additionally or alternatively, the integrated circuit may be configured to control the magnetic field of the electromagnet to allow passage of a fluid though the medical device at one or more timed intervals, such as one or more timed intervals relating to an ingestion of food or drink.

In some aspects, the medical device may include a controller, the controller including the electromagnet. For example, the controller may include a housing, the housing of the controller including the electromagnet, and optionally, an integrated circuit. The controller, e.g., the controller housing, may include an actuator such as a switch or button. Thus, in some aspects, an integrated circuit within the controller housing may be configured to control the magnetic field of the electromagnet in response to the actuator. In some aspects, the controller may be configured to be placed against a body of a patient proximate the medical device implanted within the patient. The controller may be at least partially aligned with the housing, e.g., to adjust, optimize, or otherwise control the strength of the magnetic field between the electromagnet and a metal of the medical device, such as a metallic ring or other metallic element.

Any of the elements above, e.g., the diaphragm, the metallic element(s), the valve seat (in addition to, or separate from the metallic element(s)), the sealing element, the housing, the electromagnet, the core element, the controller, the controller housing, the integrated circuit(s), and/or the sensor(s), may be used in combination with any other element, including any additional and/or alternative features, or variation of features of the elements as discussed above.

Some aspects of the present disclosure include methods of treatment. In one aspect, for example, the present disclosure includes a method of treating a patient, comprising: generating a magnetic field between an electromagnet and a medical device implanted in the patient, the medical device including: an inlet and an outlet for passage of a fluid through the medical device; a diaphragm; at least one metallic element coupled to the diaphragm, wherein the diaphragm and the at least one metallic element define a conduit; and a sealing element at least partially aligned with the conduit; wherein the magnetic field controls passage of the fluid through the medical device. In some aspects, for example, the fluid may include a fluid from a thoracic duct or cisterna chyli of the patient.

BRIEF DESCRIPTION OF THE FIGURES

The accompanying drawings, which are incorporated in and constitute a part of this specification, illustrate various exemplary embodiments and together with the description, serve to explain the principles of the disclosed embodiments.

FIGS. 5A and 5B show an exemplary device, in accordance with one or more embodiments of the present disclosure.

DETAILED DESCRIPTION

Figure 1:
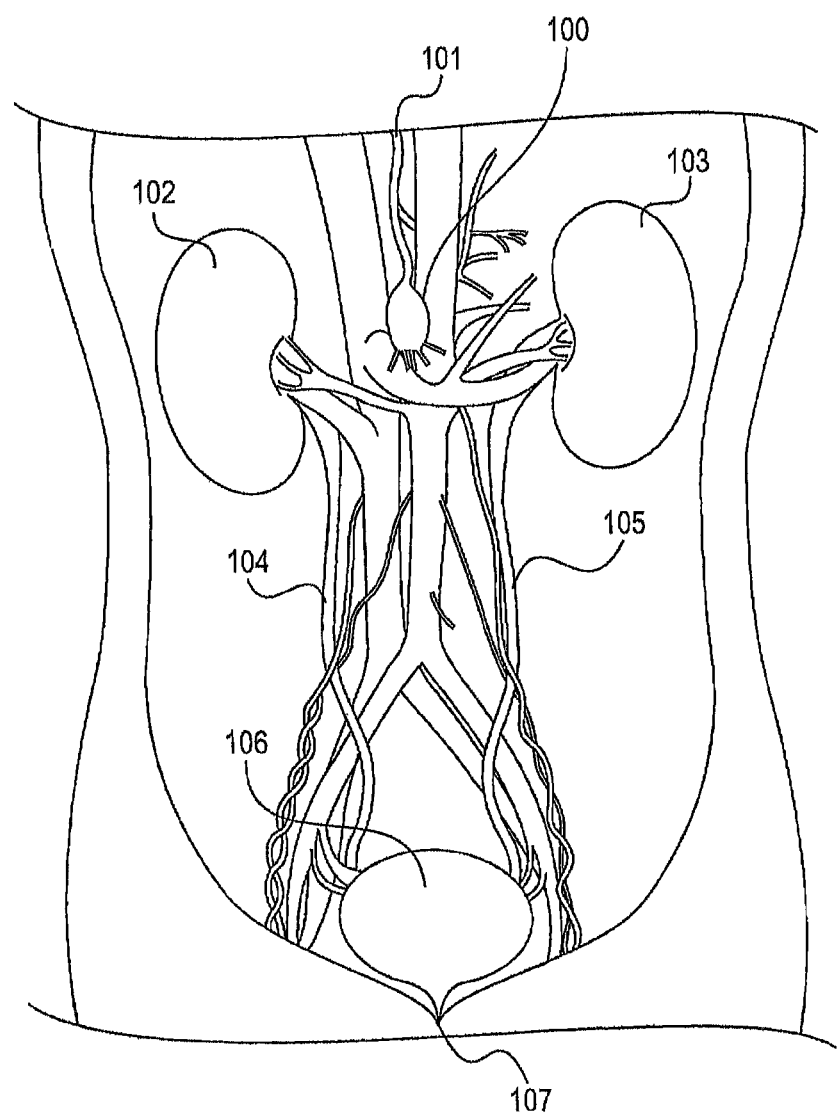
FIG. 1 shows anatomical features of the urinary and lymphatic systems.

Biochemistry of Lipids and Long Chain Fatty Acids

Dietary lipids, including, e.g., fatty acids, monoglycerides, diglycerides, triglycerides, cholesterol, and phospholipids, undergo four major processes of assimilation starting in the gastrointestinal (GI) tract. (1) The first stage, emulsification, happens in the stomach and proximal small intestine. Once lipids are ingested and pass through the stomach, they form droplets in the small intestine. Bile acids are secreted from the gallbladder and enter the GI tract at the duodenum. Bile salts then coat and decrease the surface tension of the lipid droplets, which further reduces the size of the emulsified lipid droplets. (2) The second stage, hydrolysis, occurs in the jejunum. Pancreatic enzymes such as lipase, colipase, cholesterol esterase, and phospholipase degrade lipids in the emulsified droplets into non-esterified fatty acids, monoglycerides, cholesterol, and lysophospholipids. (3) In the third stage, micelle formation, the lipid products of the hydrolysis, combine with bile acids and phospholipids to form water-soluble micelles. (4) In the fourth stage, absorption, the micelles diffuse across the apical membrane of intestinal cells called enterocytes in the jejunum.

Once inside the enterocytes of the small intestine, lipids, especially long chain fatty acids, are at least partially reprocessed and re-esterified into triglycerides and phospholipids. The esterified lipids then combine with cholesterol, other lipids, and proteins to form chylomicrons, which are lipoproteins that enable fats and cholesterol to be solubilized and transported into the bloodstream. For example, chylomicrons may comprise about 85-92% triglycerides, about 6-12% phospholipids, about 1-3% cholesterol, and about 1-2% proteins. The nascent chylomicrons thus formed in the enterocytes generally range from about 75 nm to about 1200 nm in size. These chylomicrons first are transported out of the basolateral aspect of intestinal enterocytes, and then are absorbed into lacteals, blind-end lymphatic channels present in the wall of the small intestine. Lacteals are found in the lamina propria of intestinal villi, and are contiguous with expanding lymphatic channels that drain the gut, pass through lymph nodes, and ultimately converge into a sac-like structure called the cisterna chyli (CC).

The CC is located retroperitoneal to the right of the aorta and of the spine at the ~T12-L1 vertebra level. While the CC is typically on the right, some data suggests it may be on the left in a relatively small percentage of cases. The CC generally comprises thin but strong tissue, and is surrounded by superficial fibrous tissue. Histologically, the wall of the CC is similar to a medium-sized vein with collagenous, elastic, and sparse smooth muscle composition. Endothelial cells line the lumen and a prominent internal elastic lamina is present. The size and shape of the CC may vary considerably from patient to patient. In some patients, for example, the CC is little more than a convergence of the lymphatic trunks with a minimal sac-like dilation.

As shown in FIG. 1, the thoracic duct 101 emanates from the superior aspect of the CC 100 and ascends the thoracic cavity along the right lateral spine, where it crosses to the left lateral spine and carries the lipid-laden high-calorie nascent chylomicrons into venous circulation at the left subclavian vein-internal jugular vein confluence (left venous angle). Once the chylomicrons enter the blood, they receive apolipoprotein C-II (APOC2) and apolipoprotein E (APOE) from high-density lipoproteins (HDL) to form mature chylomicrons. Once triglyceride stores in the mature chylomicrons are distributed to tissue, the chylomicrons return APOC2 to the HDL to become chylomicron remnants. Chylomicron remnants generally range from about 30 nm to about 50 nm in size. The chylomicron remnants are then available to be taken up by macrophages in the arterial wall, potentially contributing to lipid deposition in the arteries and the formation of atherosclerotic lesions.

According to embodiments of the present disclosure, a lipid-rich fluid, such as a postprandial fluid, e.g., chyle comprising chylomicrons and/or other lipid-rich components, may be redirected or shunted from the lymphatic system to prevent metabolism and absorption of the fluid and lipid calories from the fluid in the body. For example, embodiments of the present disclosure may be used in the treatment of hyperlipidemia (elevated lipid levels in the blood, including cholesterol and/or triglycerides) and/or dyslipidemia (abnormal lipid levels in the blood). In some embodiments, for example, at least a portion of a fluid may be removed from the thoracic duct 101, from the CC 100, and/or from one or more other components or portions of the lymphatic system at least temporarily and redirected for elimination from the body, thus circumventing transport of the fluid to the bloodstream. For example, the fluid may be redirected from the lymphatic system, e.g., the thoracic duct 101 and/or the CC 100, and eliminated via the urinary system or the gastrointestinal system, or may be transported from the lymphatic system directly outside the body, such as via a stoma. The lipid-rich fluid may be milky-white. Since the fluid may comprise components other than lipids that are useful and/or necessary for the patient, e.g., white blood cells, electrolytes, and/or clotting proteins, the fluid may be only temporarily redirected. For example, chyle may comprise about 10-60 g/l of total fat, about 150-250 mg/l of fibrinogen, about 10-15 g/l globulin, about 10-30 g/l albumin, and about 20-40 g/l of total protein. Chyle also may include lymphocytes, e.g., T cells, among other components. The composition of chyle may vary over time and from patient to patient, e.g., based at least in part on the amount and type of calories consumed.

According to some embodiments of the present disclosure, the fluid may be redirected from the CC 100 and/or the thoracic duct 101 (e.g., a portion of the thoracic duct such as the proximal thoracic duct) to the urinary tract via a fistula. FIG. 1 shows the posterior abdominal cavity and structures in the retroperitoneal space. For illustration purposes, the CC 100 is shown in FIG. 1 in front of the inferior vena cava (IVC) and aorta; in reality the CC 100 is located behind the IVC and just right lateral to the abdominal aorta at approximately T12-L1. The lymphatic system draining the gut is schematically represented as small connecting vessels on the bottom of the CC sac. FIG. 1 shows the CC 100 and thoracic duct 101, as well as the urinary system, including the right and left kidneys 102, 103, the right and left ureters 104, 105, the bladder 106, and the urethra 107. In the urinary tract, the kidneys 102, 103 extract bodily waste for removal as urine, which passes through ureters 104, 105 into the bladder 106 for excretion through the urethra 107. By redirecting a portion of a lipid-rich fluid from the CC 100 and/or the thoracic duct 101 into the urinary tract, e.g., via a kidney (e.g., a renal pelvis or calyx of the kidney), a ureter, or the bladder, lipids may be combined with and eliminated with urine to reduce a patient's overall caloric load. Other components in the lipid-rich fluid, e.g., cholesterol, may be eliminated from the body as well. Further, removing chylomicrons from the lymphatic system may prevent their metabolism in the blood, thus reducing or eliminating chylomicron remnants that may contribute to the buildup of fatty plaques and cholesterol in arteries and/or prevent elevated or otherwise abnormal lipid levels in the blood. Some aspects of the present disclosure therefor may provide for the prevention and/or treatment of atherosclerosis. For example, the devices and methods disclosed herein may help to prevent atherosclerosis in addition to, or as an alternative to, pharmacological treatment via the administration of statins or other drugs.

Figure 2A:
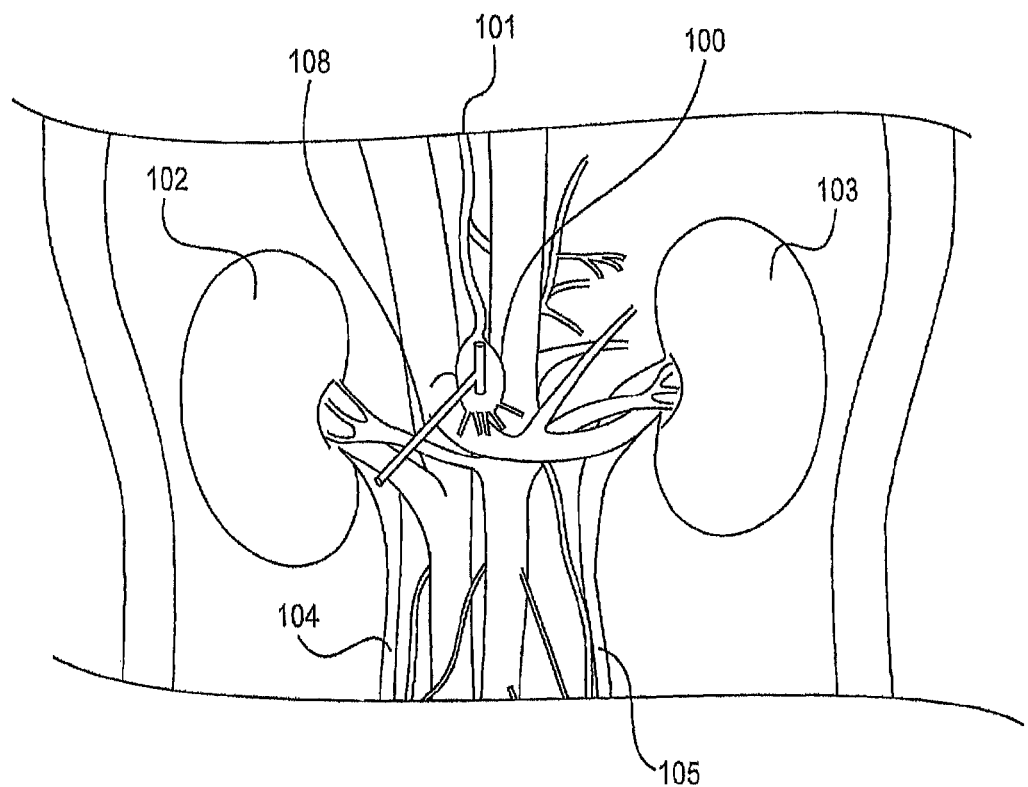
FIGS. 2A-2C illustrate exemplary embodiments of the present disclosure.

In at least one embodiment of the present disclosure illustrated in FIG. 2A, for example, the CC 100 may be connected to the right ureter 104 with device 108. Tissues of the CC 100 and of the right ureter 104 may be joined via a fistula connection with device 108. The device 108 may extend from a proximal end located within the CC 100 to a distal end located within the right ureter 104. For example, the device 108 may include a side port or other suitable channel in communication with the CC 100 and the right ureter 104. While FIG. 2A shows a fistula at or near the right renal pelvis, it is understood that the fistula may be established at any location along ureter 104. A fistula tract between the CC 100 and the left ureter 105 is also possible and encompassed by the present disclosure.

Figure 2B:
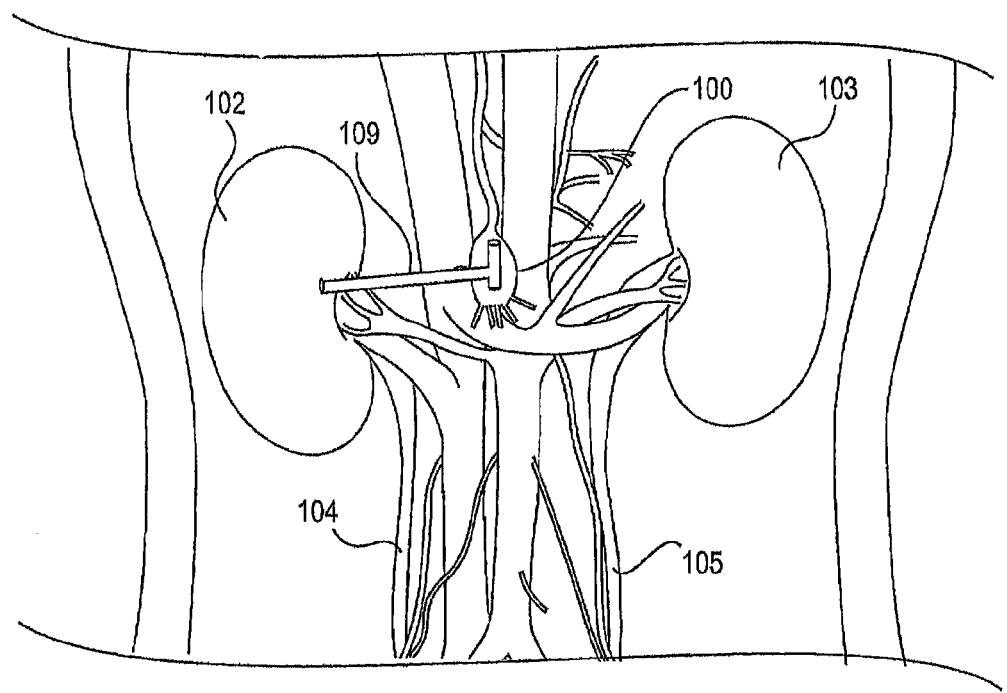

Additionally or alternatively, as illustrated in FIG. 2B, the CC 100 may be connected to the right kidney 102 with device 109. The device 109 extends from a proximal end located within the CC through a side port leading to a distal end located within the renal pelvis of the right kidney 102. A person of ordinary skill in the art would understand that a fistula could also join the CC 100 and the left kidney 103 at similar anatomic junctions (e.g., the renal pelvis or calyx).

Figure 2C:
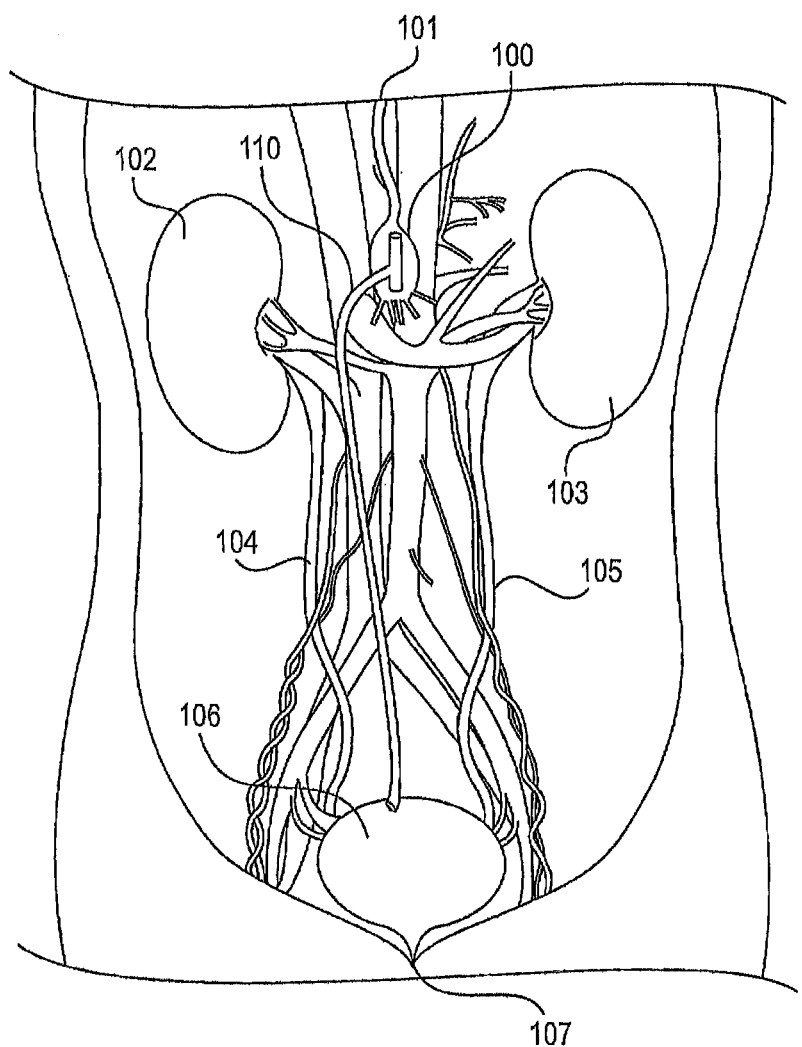

FIG. 2C shows yet another embodiment, wherein the CC 100 is connected to the bladder 106 with device 110. The device 110 extends from a proximal end located within the CC 100 through a side port leading to a distal end located within the bladder 106. Devices 108, 109, 110 shunt at least a portion of lipid-rich fluid from the CC 100 into the urinary tract. Once in the urinary tract, resorption of the lipids is prevented by the highly elastic and leak-proof urothelium, which serves as a conduit to excrete unused lipids such as chylomicrons and cholesterol with urine. This elimination may result in diminished calorie load and weight loss over time, as well as reduced amounts of chylomicrons and other lipid-containing components available for metabolism in the blood, thereby preventing buildup of plaque in the vascular system.

In some embodiments of the present disclosure, there may be multiple connections to redirect a fluid from the thoracic duct 100 and/or the CC 100, e.g., any combination of connections between the thoracic duct 101 and/or CC 100 and left and right kidneys 102, 103, left and right ureters 104, 105, the bladder 106, and outside of the body. Further, for example, one or more devices may be used to shunt or redirect at least a portion of fluid from the thoracic duct 101 to the urinary tract, e.g., as an alternative to, or in conjunction with, redirecting fluid from the CC 100 to the urinary system.

Other embodiments consistent with the present disclosure may be contemplated. For example, a ureter may be severed and the portion of the ureter leading to the bladder anastomosed directly to the CC 100, such as via a vascular graft tube or other suitable device. This type of connection may be relatively more appropriate for patients with a dysfunctional kidney, wherein severing the ureter from the dysfunctional kidney may implicate fewer health concerns. A second vascular conduit may be created to anastomose the remaining ureter stub (i.e., the portion leading from the kidney) to the other ureter. In some embodiments, fluid may be redirected from the thoracic duct 101 and/or the CC 100 to exit the body through the gastrointestinal system, e.g., via the bowel. For example, fluid may exit the body via the small bowel above the ileocecal valve.

Shunting Devices

Figure 3A:
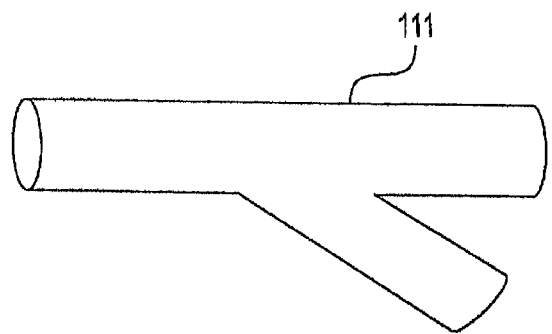
FIGS. 3A and 3B show exemplary devices, in accordance with one or more embodiments of the present disclosure.

Any suitable device for creating a fistula may be used. In some embodiments, the shunting device has a tubular structure including one or more lumens. FIGS. 2A-2C show different 3-way, T-bone type of shunting devices 108, 109, 110, similar to another exemplary 3-way shunting device 111 shown in FIG. 3A. Each of these devices 108-111 has three legs; two legs anchoring the device in the CC 100 and a third leg emanating from a side of the lumen defined by the two legs. The shunting device need not be limited to a 3-way configuration, however. Further non-limiting examples of shunting devices suitable for the present disclosure include 2-way devices, 4-way devices, e.g., H-shaped device 112 shown in FIG. 3B, and the like as known to one of skill in the art. A 2-way shunting device may simply include a cylindrical- or helical-shaped tube, for example, optionally including an anchoring mechanism as discussed below at one or both ends of the tube.

The type of shunting device chosen may include consideration for the type of tissues and strength of tissues to be joined, suitable means for attaching the device to tissue, the amount of time the shunting device is expected to remain in the patient (e.g., short-term vs. long-term), and/or the particular needs of a patient. The shunting device may be size-selectable and customizable, thus accommodating variability among patients' anatomy. Similarly, the size of the shunting device lumen(s) may vary according to the needs of the patient and decision by the patient's physician or other healthcare provider.

The shunting device may comprise one or more biocompatible, elastic, and/or flexible materials. Exemplary materials include, but are not limited to, silicone (e.g., silicone rubber or medical grade silicone), one or more polymers such as styrene-isobutylene-styrene (SIBS), polypropylene, polyurethane, or a fluoropolymer, and metals or metal alloys including, e.g., metal in the form of coils, magnets, and/or braided wire. In some embodiments, the shunting device may include flexible inner coils or coaxial coils optionally coated with a polymer coating such as GORE™ PTFE-covered coils. The shunting device may be flexible, for example including flexible scaffolding. Device 110 of FIG. 2C includes, for example, a flexible portion joining the CC 100 to the bladder 106. In some embodiments, the material (s) may be chosen to accommodate one or more fenestrations in the material(s).

Further, the shunting device may include a bioresorbable material that dissolves or erodes over time. For example, in some embodiments, at least a portion of the shunting device includes a bioresorbable material that dissolves over a predetermined time, such as from several days or weeks to several months. In some embodiments, substantially all of the shunting device may be bioresorbable. In some embodiments, the shunting device may include a material that permits tissue ingrowth. The material may be arranged in a scaffolding to permit tissue ingrowth along and/or inside of the shunting device, such as at the point of attachment to a tissue surface or anchoring to a tissue wall. In some embodiments, the shunting device may include both a bioresorbable material and a material that permits tissue ingrowth such that tissue supports the fistula as the bioresorbable material erodes over time. Such devices may, for example, be suitable for short-term implantation and remove a need to surgically remove the device. The shunting device may also include a tissue graft, e.g., human, animal, or man-made tissue, such as isogeneic tissue or allogeneic tissue, e.g., a portion of the saphenous vein or other suitable tissue. In some embodiments, for example, the shunting device may include a graft comprising tissue from the patient in whom the device may be implanted, or tissue from a suitable donor. One or more stents may also be used to support and/or expand a fistula connection according to the present disclosure including, e.g., covered stents, Nitinol stents, or plastic stents.

The shunting device may further include a pharmaceutical drug or other therapeutic agent for release in the body. Delivery of the pharmaceutical or therapeutic agent may be effected, for example, through a porous material of the shunting device, or embedding the pharmaceutical or therapeutic agent in a bioresorbable material of the shunting device to be released over time.

Anchoring Mechanism

In some embodiments, the shunting device includes at least one anchoring mechanism. The anchoring mechanism may include one or more means of attaching the shunting device to a tissue surface wall. The anchoring mechanism may also assist in anastomosis, for example, and/or securing the shunting device in the body for short-term or long-term implantation. In some embodiments, the anchoring mechanism may include use of one or more materials for attaching or sealing the shunting device to a tissue surface. Examples of anchoring mechanisms include, but are not limited to, staples, sutures, a flange/flared configuration at the end of one or more legs, an expandable collar or basket configuration at the end of one or more legs, a grafting surface, fibrin sealants, hydrogel matrices, extended tines, magnets, or any other means of connecting two body organs.

In some embodiments, the shunting device includes one or more flared openings to assist in anchoring the shunting device within an anatomical location, e.g., the CC and/or kidney, ureter, or bladder. For example, the shunting device may include a circumferential flap, e.g., for opening and securing the shunting device at a desired anatomical location. In some embodiments, the fistula may be established by adhering the shunting device to the exterior tissue surface of the organ, while in other embodiments, the shunting device may adhere inside of the organ. Further, the shunting device may have a linear or curved (e.g., helical) portion disposed within the CC, kidney, ureter, and/or bladder having sufficient length to keep the shunting device in place. A junction between the shunting device and the tissue surface (e.g., an inner and/or outer surface) may be sealed with a suitable material such as a fibrin sealant or hydrogel. In some embodiments, at least a portion of the shunting device in contact with the tissue surface may include a mesh material to facilitate sealing the shunting device to the tissue surface.

In at least one embodiment, the shunting device may include an expandable basket or basket-like component for anchoring the device within an anatomical location. For example, one or more legs of the shunting device may be coupled to an expandable basket or have an expandable basket-like configuration. In some embodiments, for example, the basket may be self-expandable, e.g., comprising Nitinol. In some embodiments, the basket may be manually expanded, e.g., via a control wire or other suitable mechanism. In at least one embodiment, for example, a control wire may extend through the lumen of the shunting device and couples to a self-expandable cage-like metal wire structure having an open mesh to permit fluid flow. The structure may be initially in a collapsed configuration within the lumen at an end of the lumen. The leg of the shunting device may be inserted into an opening (e.g., an opening created in the CC, the thoracic duct, the left or right kidney, the left or right ureter, or the bladder) with the structure in the collapsed configuration. Once placed in the opening, the structure may be expanded against the walls of the opening to anchor the shunting device. The structure may expand within the opening and/or may expand against tissue internal to the organ or duct in which it is inserted.

In some embodiments, the shunting device may include two magnets. For example the shunting device may include a first magnetic portion coupled to the wall of the CC and a second magnetic portion coupled to ureter, kidney (e.g., renal pelvis) or bladder, wherein connecting the two magnetic portions creates a fistula connection. Each magnetic portion may be separately introduced for implantation, e.g., via antegrade delivery through the urethra and retrograde delivery through a vein, or also may be introduced together for implantation. The first and/or second magnetic portions may include a magnet disposed circumferentially around a lumen through which a fluid may flow, e.g., a hollow magnet tube. In some embodiments, for example, a magnet tube may be attached to a tissue surface, wherein an opening in the tissue surface is created by perforating through a portion of tissue adjacent to the inner lumen of the magnet tube. Further, any of the above anchoring mechanisms may be used in combination, such as a flared opening including magnets, a circumferential flap including sutures or tines, or a grafting surface including sutures (e.g., bioabsorbable sutures).

FIGS. 2A-2C show shunting devices 108, 109, and 110 with a proximal longitudinal portion (e.g., a leg) disposed within the CC to assist in anchoring. In case the shunting device establishes a passageway from the CC to outside of the body (ostomy), the shunting device may include an anchoring mechanism to secure the shunting device to the body surface and accordingly allow fluid to flow from the CC to exit the body into an appropriate receptacle that can be removed and replaced. The anchoring mechanism may further include a locking mechanism to lock the shunting device to the body surface to secure it in place.

Control Mechanism

Figure 3B:
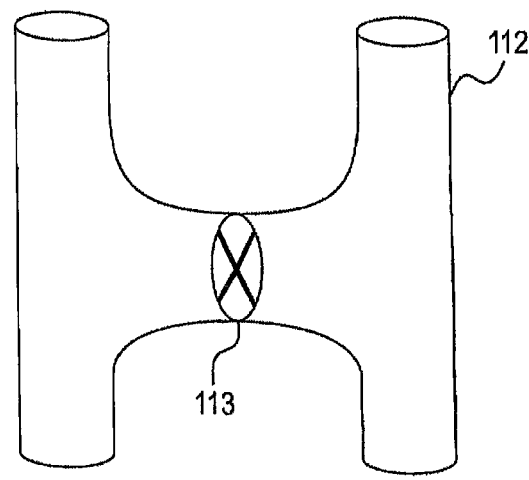

The shunting device may include at least one control mechanism to regulate fluid flow and/or separate different fluid components, illustrated in FIG. 3B as control mechanism 113 of shunting device 112. In some embodiments, the shunting device may include more than one control mechanism, for example two, three, or more control mechanisms, which may be the same or different from one another. The control mechanism may include one or more valves. Non-limiting examples of control mechanisms that may be used according to the present disclosure include diaphragm valves, slitted valves, duckbill valves, elastomeric valves, one-way valves (e.g., check valves, including zero pressure valves), apertures (e.g., a small aperture to restrict flow), and lumens having an hour-glass shape. For example, a portion of the shunting device may include a plurality of perforations or holes ranging from about 5 microns to about 500 microns, such as from about 5 microns to about 50 microns, from about 50 microns to about 500 microns, from about 100 microns to about 500 microns, or from about 250 microns to about 500 microns to assist in controlling or regulating a fluid flow rate. In some embodiments, the size of the holes may be selected to separate one or more components from other components within the fluid, such as separating white blood cells from chylomicrons, or vice-versa.

In at least one embodiment, the shunting device may include a diaphragm valve, optionally in combination with one or more other control mechanisms. For example, a first portion of the shunting device may include a diaphragm valve and a second portion of the shunting device may include a plurality of perforations or holes to direct and facilitate flow of a fluid from the CC into a lumen of the device. The control mechanism(s) may be located at various positions within the shunting device, such as at or near an opening or end of the shunting device, or at any location between openings. The control mechanism may include one or more inorganic and/or organic biocompatible materials, such as polymers, metals, metal alloys, ceramics, minerals, and/or human or non-human tissue.

The control mechanism may regulate a fluid flow mechanically, electronically, magnetically, osmotically, and/or ionically, and may be configured for active control (e.g., to enable a patient, healthcare provider, software program or application, etc., to adjust fluid flow) and/or passive control (e.g., to regulate a rate of fluid flow depending on pressure, particulate size, molecular weight, molecular mass, lipophilicity, diffusion, other physical, chemical or physiological phenomena, and/or other design of the control mechanism). The control mechanism may be adjusted or controlled manually or remotely, for example by communication with a remotely-located or mobile device such as a sensor, a laptop computer, a desktop computer, a tablet computer, a smart phone, a smart watch, or any other suitable electronic device. The control mechanism may be adjusted or controlled according to pre-programmed or pre-set parameters, and/or according to inputs from a user such as a physician or other healthcare provider, or from the patient or other user. In some embodiments, for example, the control mechanism may be used to regulate the amount of caloric loss and/or cholesterol levels of a patient. In some embodiments, the control mechanism additionally or alternatively may regulate the amount of white blood cell loss of a patient.

The control mechanism may include two or more separate components coupled together or in wireless communication with one another. For example, the control mechanism may include a first component implanted in the body (e.g., in direct contact or otherwise coupled to a shunting device as discussed above) and a second component located outside the body, wherein the second component may be in proximity of the first component. For example, the second component may rest on or near an external surface of the body, e.g., adhered to the skin with a biocompatible adhesive material or secured to the body via a strap or other suitable mechanism, and/or may be brought in proximity of the first component only temporarily and as needed to communicate with the first component. In some embodiments, the control mechanism may include only one component, e.g., a valve implanted in the body.

Figure 4A:
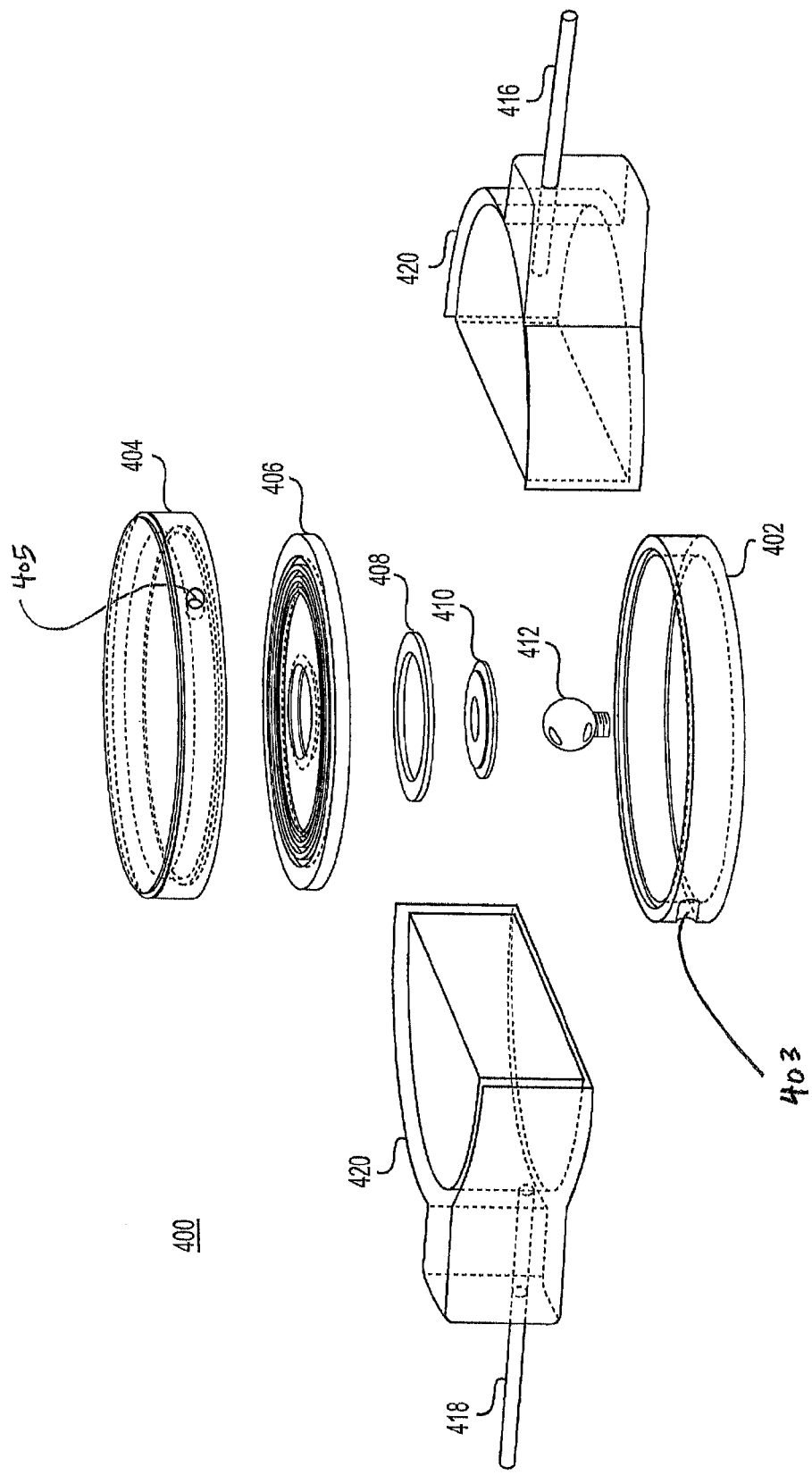
FIGS. 4A and 4B show an exemplary device, in accordance with one or more embodiments of the present disclosure.
Figure 4B:
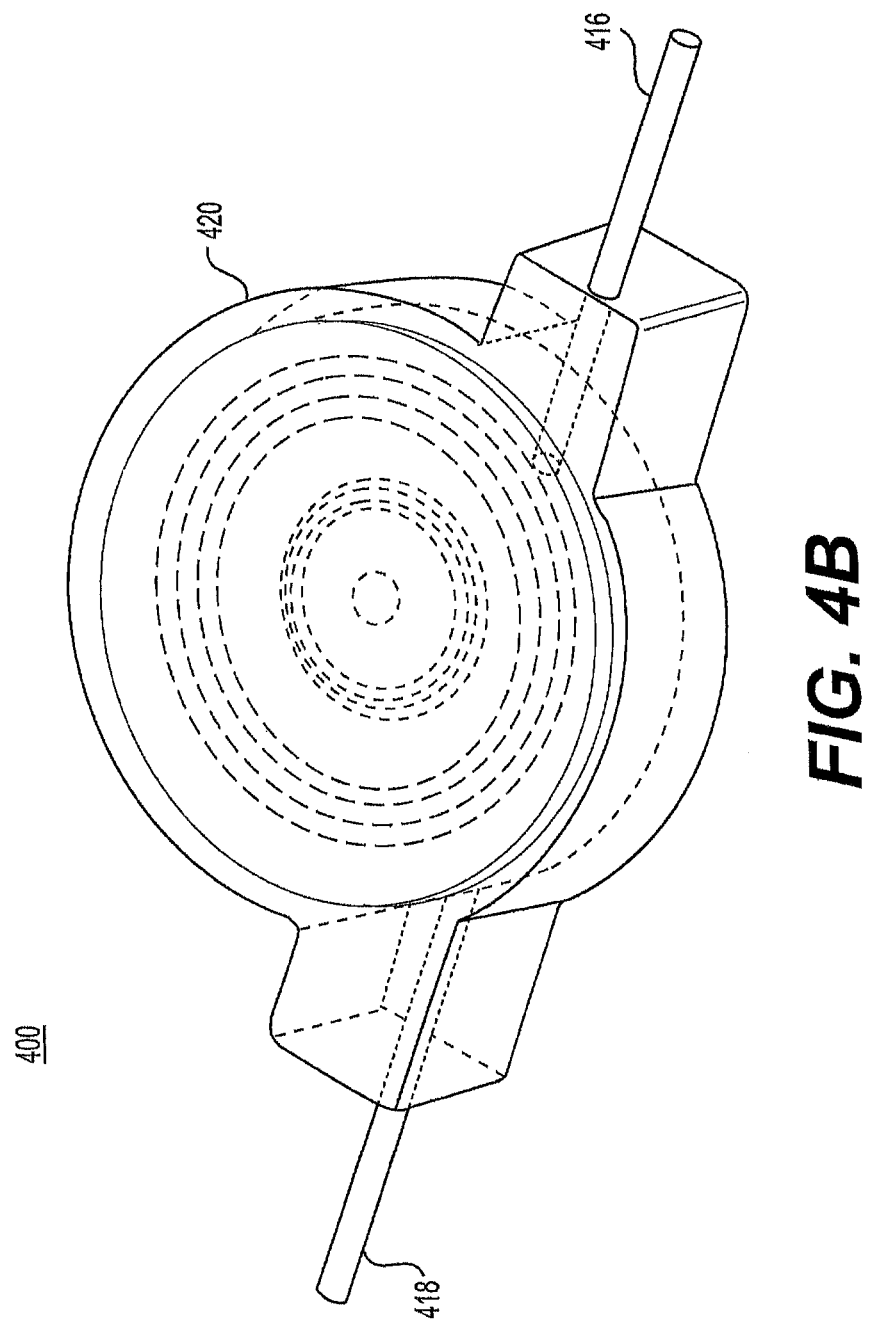
Figure 5B:
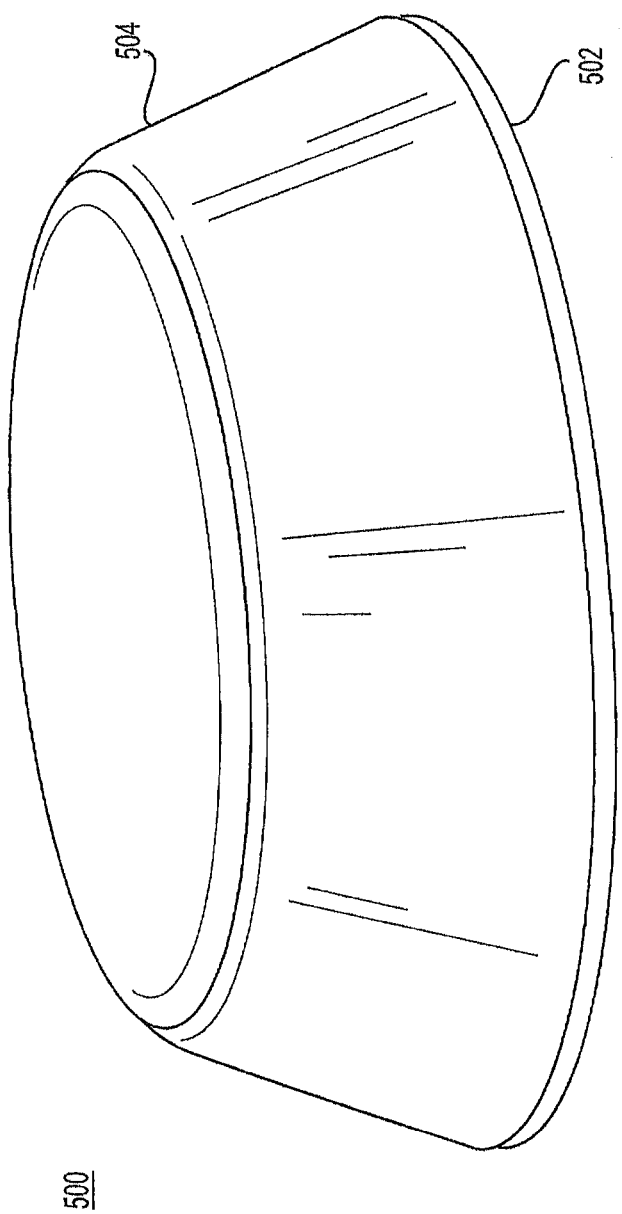

FIGS. 4A-4B show exploded and assembled views, respectively, of an exemplary valve 400 (e.g., first component) for implantation within the body, and FIGS. 5A-5B show exploded and assembled views, respectively, of an exemplary controller module 500 (e.g., second component) for controlling the valve 400. FIGS. 6A-6B and 7A-7B illustrate other exemplary control mechanisms in accordance with the present disclosure, as discussed below. Any features of one control mechanism may be combined with any features of any other control mechanism. Medical devices according to the present disclosure need not include each or every feature or element discussed in connection to the control mechanisms shown in FIG. 4A-4B, 5A-5B, 6A-6B, or 7A-7B, and/or may include additional or alternative features or variations thereof. Other combinations of the elements and features shown and discussed in connection to the control mechanisms described herein also are possible without departing from the present disclosure, including any combination of the various elements and features shown in FIGS. 4A-4B, 5A-5B, 6A-6B, and 7A-7B with any other elements or features.

As shown in FIG. 4A, valve 400 may include a lower housing 402, an upper housing 404, a cover 420, a diaphragm 406, a metallic ring 408, a valve seat 410, and a sealing element 412. The terms "upper" and "lower" are used herein for convenience in referring to the figures, and do not limit the devices to any particular orientation. For example, the upper housing 404 may be above, below, to the left, or to the right of the lower housing 402, depending on the orientation of the valve 400 when implanted. The lower housing 402 and upper housing 404 enclose diaphragm 406, metallic ring 408, valve seat 410, and sealing element 412. The valve 400 may include a cover 420 that at least partially encloses the lower housing 402 and the upper housing 404. According to some aspects of the present disclosure, the valve may not include a cover 420. The lower housing 402 and upper housing 404 may be coupled together via any suitable mechanism, such as, e.g., friction fit, screw threads, mechanical locks, or adhesive, and may be detachable or permanently attached. While FIG. 4A shows separate lower and upper housing components 402, 404, in some embodiments, the housing may comprise a single integral element. Likewise, the cover 420 may include separate components or a single, integral piece. The upper housing 404 may include a first opening 405 in communication with an inlet 416, and the lower housing 402 may include a second opening 403 in communication with an outlet 418, e.g., to allow a fluid to flow through the valve from the inlet 416 to the outlet 418. In some embodiments, the direction of fluid flow may be reversed, such that fluid enters through the second opening 403 in the lower housing 402 and exits through the first opening 405 in the upper housing 404. The inlet 416 and/or outlet 418 may include a control mechanism such as a one-way valve to prevent fluid from flowing in an opposite or undesired direction, e.g., from the outlet 418 into the valve 400 and/or to the inlet 416. For example, a check valve may be placed within the outlet 418 to prevent fluid from flowing back up through the valve 400 when the valve 400 is open.

The lower and upper housings 402, 404 may comprise any biocompatible material such as, e.g., one or more polymers, metals, metal alloys, ceramics, minerals, or any combination thereof. The inlet 416 and/or outlet 418 may be in communication with one or more portions of a shunting device that are anchored to tissue as described above, e.g., to redirect fluid through the shunting device via the valve 400. In some embodiments, the inlet 416 and/or the outlet 418 may be anchored to tissue, e.g., as part of the shunting device.

The diaphragm 406 may comprise one or more flexible materials, such as silicone, polyurethane, or other flexible polymers or materials. For example, the diaphragm 406 may flex and move, e.g., towards and away from the upper housing 404. The metallic ring 408 may comprise one or more metals or metal alloys. In some embodiments, the metallic ring 408 may comprise a metal attracted by an electromagnet such as, e.g., a ferrous material such as iron or an iron alloy, or a permanent magnet. The valve seat 410 and/or sealing element 412 may comprise any suitable biocompatible material such as, e.g., one or more polymers, metals, metal alloys, ceramics, minerals, or any combination thereof. In some embodiments, the valve seat 410 and/or sealing element 412 may comprise a rigid material, such as a hard plastic, metal or metal alloy (e.g., titanium, iron, stainless steel), ceramic, or mineral (e.g., sapphire).

The diaphragm 406, metallic ring 408, and valve seat 410 may be coupled together, e.g., temporarily or permanently attached, to allow them to move as a single unit. In some embodiments, the metallic ring 408 may be at least partially or entirely covered by a material, or may be imbedded in a medium to isolate it from contact with fluid or air. For example, the metallic ring 408 may be covered and/or embedded in a biocompatible material comprising one or more polymers or copolymers (e.g., epoxy resins, polyimides, plastics, etc.), composite coatings, ceramic materials, and/or metals, such as metal plating. The metallic ring 408 may be coupled to the diaphragm 406 and/or valve seat 410, e.g., by friction fit, or bonded or otherwise attached via a bonding or adhesive agent such as glue. Similarly, the valve seat 410 may be coupled to the diaphragm 406 and/or metallic ring 408, e.g., by friction fit or via a bonding or adhesive agent. In some embodiments, the diaphragm 406, metallic ring 408, and/or valve seat 410 may have a surface feature complementary to a surface of an adjacent component, e.g., to allow the surfaces to lie flush.

The diaphragm 406, metallic ring 408, and valve seat 410 each may include an aperture, with the apertures at least partially or completely aligned, e.g., to allow a fluid to pass therethrough. While FIG. 4A shows each of the diaphragm 406, metallic ring 408, and valve seat 410 as being circular in shape and concentric with a central circular aperture, other shapes such as polygonal and/or aperture locations are possible. The sealing element 412 may be coupled to the lower housing 402 via any suitable connection, and may be aligned with the apertures of the diaphragm 406, metallic ring 408, and valve seat 410. Thus, the sealing member 412 may contact a lower surface of the valve seat 410 to block the apertures, e.g., by forming a seal with the valve seat 410. The sealing element may comprise a ball or have any other suitable shape. In some embodiments, the sealing element 412 may include a threaded portion complementary to screw threads within the lower housing 402 for coupling the sealing element 412 to the lower housing 402. In at least one embodiment, the position of the sealing element 412 with respect to the valve seat 410 and/or lower housing 402 may be adjusted, for example, to adjust the relative force exerted onto the valve seat 410/metallic ring 408/diaphragm 406 subassembly, e.g., to provide an initial or default setting of the valve 400 when inactive. By adjusting the initial position of the sealing element 412, the amount of magnetic force required to open and close the valve 400 may be controlled.

The valve 400 may have a closed configuration to prevent fluid from flowing therethrough, and an open configuration to allow fluid to flow, e.g., between the inlet and outlet 416, 418. In the closed configuration, the sealing element 412 may block the aperture of the valve seat 410 (e.g., also blocking the apertures of the metallic ring 408 and diaphragm 406) to prevent fluid flow between the upper and lower housings 402, 404. In some embodiments, the valve 400 may be in a closed configuration when not activated, e.g., in a default setting. The valve 400 may be opened or activated, e.g., by moving the diaphragm 406, metallic ring 408, and valve seat 410 toward the upper housing 404 and away from the sealing element 412 and lower housing 402. In some embodiments, for example, an electromagnet proximate the upper housing 404 may attract the metallic ring 408, thus causing the diaphragm 406, metallic ring 408, and valve seat 410 to move toward the upper housing 404 to open space between the valve seat 410 and sealing element 412. Adjusting the strength of the attraction between the electromagnet and the metallic ring 408 may adjust the size of the passageway through the valve 400 to control the rate of fluid flow through the valve 400.

At least a portion of the valve 400 may include a material and/or coating such as an antithrombic coating configured to prevent components of the fluid (e.g., clotting agents or thrombotic materials) from becoming deposited within the valve 400 over time. For example, the inside of the valve 400 may have a hydrophobic surface to prevent build-up of biological material from fluid flowing through the valve 400. In some embodiments, one or more of the lower housing 402, the upper housing 404, the inlet 416, the outlet 418, the diaphragm 406, the metallic ring 408, the valve seat 410, and the sealing element 412 may comprise a polymer or polymer mixture. Non-limiting examples of polymers and polymer coatings include silicone, polyp-xylylene) polymers such as Parylene C, and polyethylene glycol. For example, a surface within the valve 400 may be functionalized with a polymer such as polyethylene glycol to inhibit or prevent build-up of biological material. In at least one embodiment, an inner portion of the lower housing 402 and/or upper housing 404 may include a polymer or polymer coating, and the sealing element may comprise sapphire. Additionally or alternatively, the inside of the valve 400 may include one or more active agent(s) to interact with the biological material and prevent build-up within the valve 400. In some embodiments, for example, a surface within the valve may be coated with an anticoagulant such as heparin and/or a zwitterion molecule.

While FIG. 4A shows the metallic ring 408 disposed between the valve seat 410 and the diaphragm 406, in some embodiments the valve seat 410 may be disposed between the metallic ring 408 and the diaphragm 406. Further, some embodiments may not include a metallic ring 408, for example if the valve seat 410 comprises one or more metals, such as iron or other metal(s), attracted by an electromagnet.

Such an electromagnet may be generated within a component external to the body, such as controller module 500 shown in FIGS. 5A-5B. As shown in FIG. 5A, the controller module 500 may include a lower housing 502, an upper housing 504, an integrated circuit 506, a power source 508, and a coil 510. The lower housing 502 and upper housing 504 enclose the integrated circuit 506, power source 508, and coil 510. In some embodiments, the controller module 500 may further include a core element 512. While the controller module 500 as shown is generally frustoconical, other shapes may be suitable such as, e.g., cylindrical, spherical, rectangular, etc. The lower housing 502 and upper housing 504 may be coupled together via any suitable mechanism, such as, e.g., friction fit, screw threads, mechanical locks, or adhesive, and may be detachable or permanently attached. The lower and upper housings 502, 504 may comprise any biocompatible material such as, e.g., one or more polymers, metals, metal alloys, ceramics, minerals, or any combination thereof. In some embodiments, the controller module 500 may include a single integral housing rather than separate components 502, 504.

The power source 508 may generate power according to any suitable methods known in the art. For example, the power source 508 may provide power via an electrolytic cell, a solar cell, or any other device or method for harvesting energy. In some embodiments, the power source 508 may comprise a self-contained power unit such as a rechargeable or non-rechargeable battery. The controller module 500 may be configured to allow a user to remove, replace, and/or recharge the power source 508.

The power source may be coupled to the coil 510 for generating a magnetic field. The coil 510 may comprise any suitable metallic material, such as wire, shaped into a coil configuration. The wire may be insulated, e.g., comprising polymer coating. In some embodiments, the coil 510 may comprise insulated copper wire. To increase the strength of the electromagnet and magnetic field, some embodiments of the present disclosure may include a core element 512 disposed inside a circumference of the coil 510, e.g., centered inside the coil 510. The core element 512 may comprise a metal or metal alloy, for example iron or an iron alloy. The core element 512 may be optional, however.

The controller module 500 may control (e.g., open and close) the valve 400 by turning the power source 508 on, thus generating a magnetic field from the electromagnet (e.g., the power source 508 and coil 510, or the power source 508, coil 510, and core element 512) to attract metal within the valve 400, such as the metallic ring 408. Turning the power source 508 off may terminate the magnetic field, allowing the metal within the valve 400 to return to its original position. For example, in some embodiments, turning the power source 508 on may cause the valve 400 to open, and turning the power source 508 off may cause the valve 400 to close. Depending on the configuration of the valve 400 with respect to the controller module 500 and/or electromagnet, turning the power source 508 on may cause the valve 400 to close, and turning the power source off may cause the valve 400 to open. Adjusting the strength of the magnetic field may cause the valve 400 to partially close and/or partially open, thus adjusting the rate of fluid flow through the valve 400.

The controller module 500 may be in proximity of the valve 400 to allow for sufficient magnetic attraction between the controller module 500 and the valve 400. In some embodiments, for example, the controller module 500 may be at least partially aligned with the valve 400, e.g., aligned with a metal within the valve 400, such as the metallic ring 408. In some embodiments, a central axis of the controller module 500 may aligned with a central axis of the valve 400, e.g., such that the coil 510 is centered around the metallic ring 508. While FIGS. 5A-5B illustrate an exemplary controller module 500 to generate an electromagnet outside the body, in some embodiments, the controller module 500 may be implantable, e.g., adjacent to the valve 400. Further, in some embodiments, an electromagnet may be generated inside the body, such as coupled to the valve 400, e.g., coupled to the upper housing 404. In such cases, the electromagnet may include an implantable power source, e.g., also coupled to the valve 400 to generate a magnetic field.

The controller module 500 may include one or more integrated circuits 506 configured to control and/or receive information from one or more electronic components, such as the power source 508, a sensor located inside or outside of the body, and/or any other electronic components or devices, such as computing devices. Suitable types of integrated circuits 506 according to the present disclosure may include, but are not limited to, analog, digital, and mixed signal integrated circuits, application-specific integrated circuits (ASICs), and microprocessors.

The integrated circuit 506 may switch on (and off) power to the coil 510 via the power source 508, creating an electromagnet to open the valve 400 by attracting a metallic material, e.g., ferrous material, of the metallic ring 408 coupled to the diaphragm 406. When the power is turned off, the valve 400 may return to its closed state. The integrated circuit 506 may control the valve 400 according to one or more parameters that may be pre-programmed into the integrated circuit 506, dynamically detected by the valve 400 and/or the controller module 500, and/or manually adjusted via a suitable user interface, e.g., coupled to the controller module 500 or in wireless communication with the controller module 500.

In some embodiments, the integrated circuit 506 may include a timer or timing element for opening and closing the valve 400 at timed intervals. In some embodiments, for example, the integrated circuit 506 may be configured to communicate with the valve 400 according to a pre-set algorithm, such as instructing the valve 400 to open and close at regular time intervals (e.g., at prescribed times preceding, during, and/or following ingestion of food or drink).

In some embodiments, the integrated circuit 506 may communicate with one or more sensors implanted in the body and connected to the circuit thru a wire and catheter, and/or may communicate with one or more sensors outside or inside the body wirelessly, such as via radio frequency (RF) wireless communication. In some embodiments, for example, the integrated circuit 506 may be configured to receive information regarding physiological parameters or conditions within the body, such as detecting the presence or absence of fluid, flow rate, pressure, temperature, or pH, among other parameters or stimuli. For example, an increase in the amount of fluid or reaching a threshold amount of fluid may prompt the controller module 500 to instruct the valve 400 to open. Similarly, a decrease in the amount of fluid or falling below a threshold may prompt the controller module 500 to instruct the valve to close.

In some embodiments, the integrated circuit 506 may receive information manually via a switch or other actuator activated by a user, such as a physician, technician, or the person having the implanted valve 400 and wearing the controller module 500. In some embodiments, the controller module 500 may accept user inputs locally and/or remotely for operating the valve 400. For example, a user may touch a screen, press a button, flip a switch, or turn a dial on the controller module 500 to cause the controller module 500 to communicate with the valve 400 and instruct the valve 400 to open or close. In some embodiments, the controller module 500 may include an override function allowing user input to override pre-set algorithms or programs, and/or a safety mechanism to prevent user input from interfering with pre-set algorithms or programs.

Figure 6A:
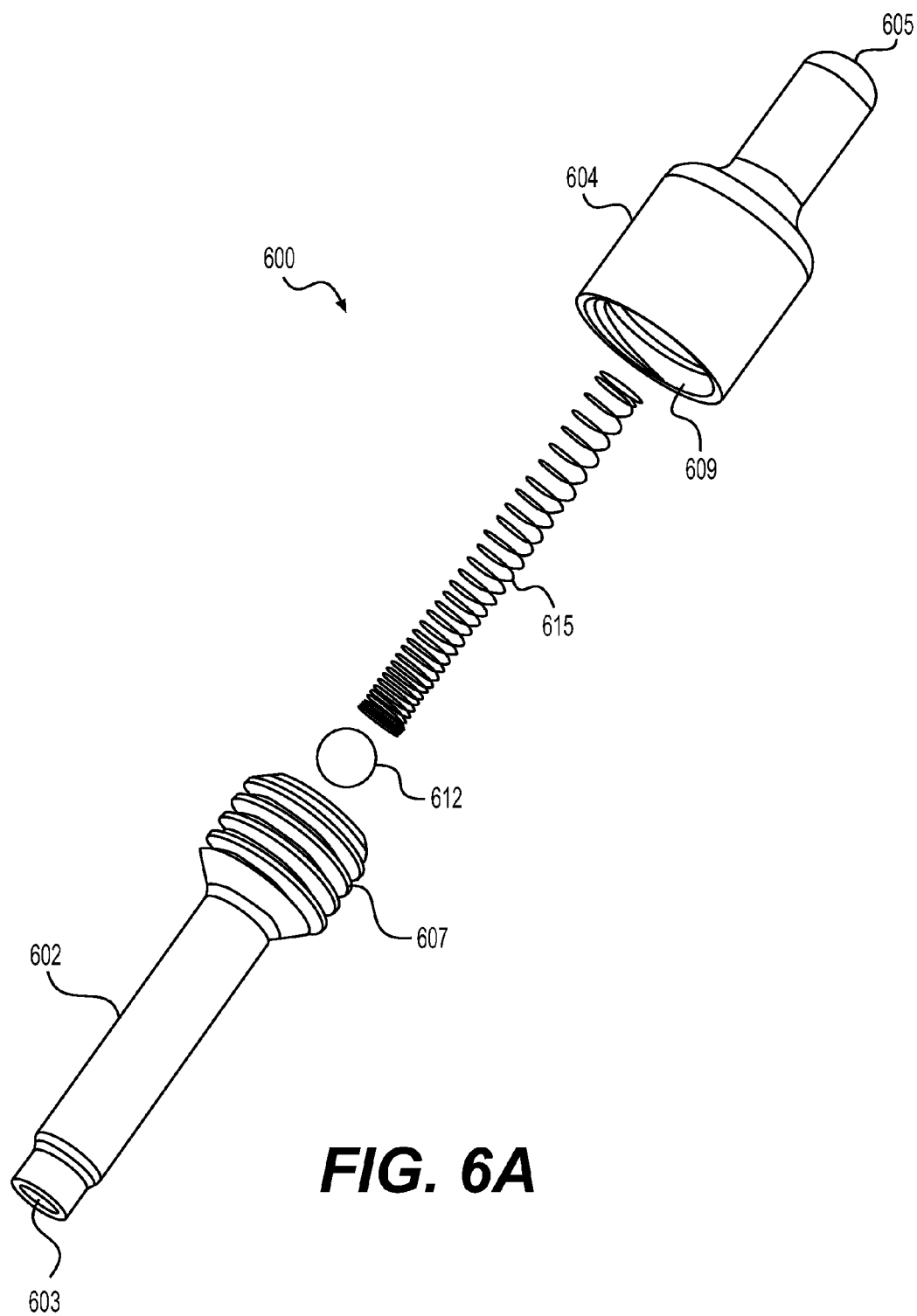
FIGS. 6A and 6B show an exemplary device, in accordance with one or more embodiments of the present disclosure.
Figure 6B:
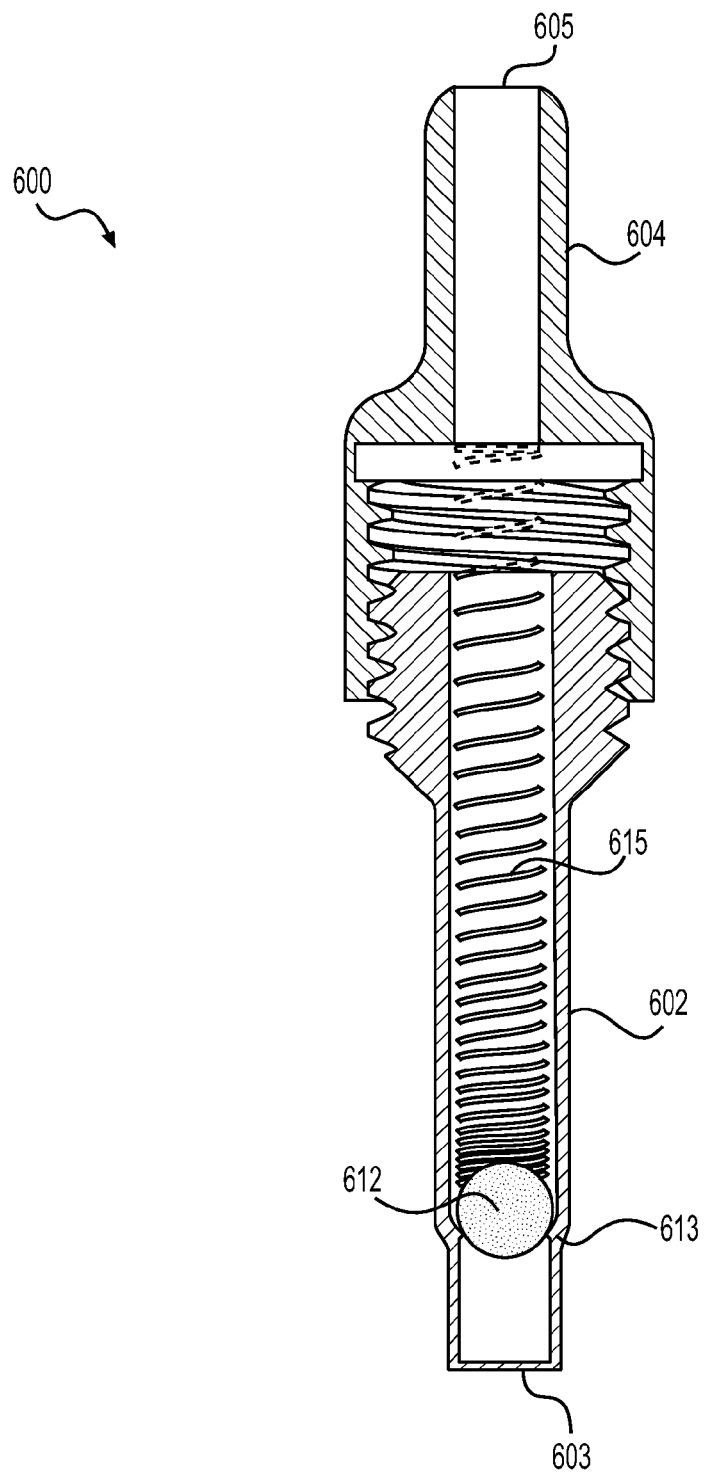

FIGS. 6A-6B illustrate another exemplary valve 600 according to some aspects of the present disclosure. The valve 600, shown in exploded view in FIG. 6A, may include a lower housing 602 coupled to an upper housing 604 via any suitable mating elements or other coupling mechanism. As shown, for example, the lower housing 602 may include a threaded portion 607 complementary to a threaded portion 609 of the upper housing 604. Other suitable coupling mechanisms may include, e.g., friction fit, mechanical locks, or adhesive. Each of the lower housing 602 and the upper housing 604 may define a passageway therethrough that together define a lumen of the valve 600, the lumen extending from a first opening 603 of the lower housing 602 to a second opening 605 of the upper housing 604.

The valve 600 also may include a sealing element 612 and a spring 615 disposed within the lumen of the valve 600. Each of the lower housing 602, upper housing 604, sealing element 612, and spring 615 may comprise any biocompatible material such as, e.g., one or more polymers (including plastics), metals, metal alloys, ceramics, minerals, or any combination thereof. In some embodiments, for example, each of the housings 602, 604 may comprise a polymer, the spring 615 may comprise a metal or a polymer, and the sealing element 612 may comprise a rigid material, such as a hard plastic, a metal or metal alloy (e.g., titanium, iron, stainless steel), a ceramic, or a mineral (e.g., sapphire). In some embodiments, the valve 600 may be safe for use in a magnetic resonance imaging (MRI) procedure, e.g., may not comprise any metals or metal alloys.

The lower housing 602 may include a valve seat 613, shown in FIG. 6B as a narrowed region of the lumen proximate the first opening 603. The sealing element 612 may be adjacent to, and moveable relative to, the valve seat 613, such that the sealing element 612 may partially or completely block fluid flow through the valve 600 by pressing against the valve seat 613. The sealing element 612 may have a rounded, spherical shape like a ball, or any other shape suitable for establishing a seal against the valve seat 613. When the lower and upper housings 602, 604 are coupled together, shown in cross-sectional view in FIG. 6B, the spring 615 may be compressed. In some embodiments, for example, the lumen of the valve 600 may narrow proximate the second opening 605 to prevent the spring 615 from passing through the second opening 605. In some embodiments, the end of the spring 615 pointing towards the second opening 605 may be fixed to the upper housing 604 to confine the spring 615 within the lumen.

When compressed, the spring 615 may in turn press the sealing element 612 against the valve seat 613 to restrict fluid flow through the valve 600. The compressive force or tension of the spring 615 may be adjusted by moving the housings 602, 604 closer together (increasing tension) and farther apart (decreasing tension), e.g., by screwing and unscrewing the threaded portions 607, 609. Thus, fluid flow through the valve 600 may be decreased by moving the housings 602, 604 together, thus increasing the tension of the spring 615 to press the sealing element 612 with greater force against the valve seat 613. Similarly, fluid flow may be increased by moving the housings 602, 604 away from each other, thus decreasing the tension of the spring 615 to reduce the force exerted by the sealing element 612 against the valve seat 613.

The tension of the spring 615 may be adjusted to provide an appropriate preload or opening pressure of the valve 600, such that fluid entering through the first opening 603 may push the sealing element 612 off of the valve seat 613 to at least partially open the valve 600. In the absence of fluid, however, the sealing element 612 may contact the valve seat 613 to close the valve 600. The amount of fluid permitted to flow through the valve 600 may depend on the tension of the spring 615 and the force with which fluid presses against the sealing element 612 to open the valve 600. The valve 600 therefore may provide for passive control of fluid flow, e.g., based on the preload of the valve 600, and the presence and amount of fluid present (e.g., lipid-rich fluid generated by the lymphatic system).

Figure 7A:
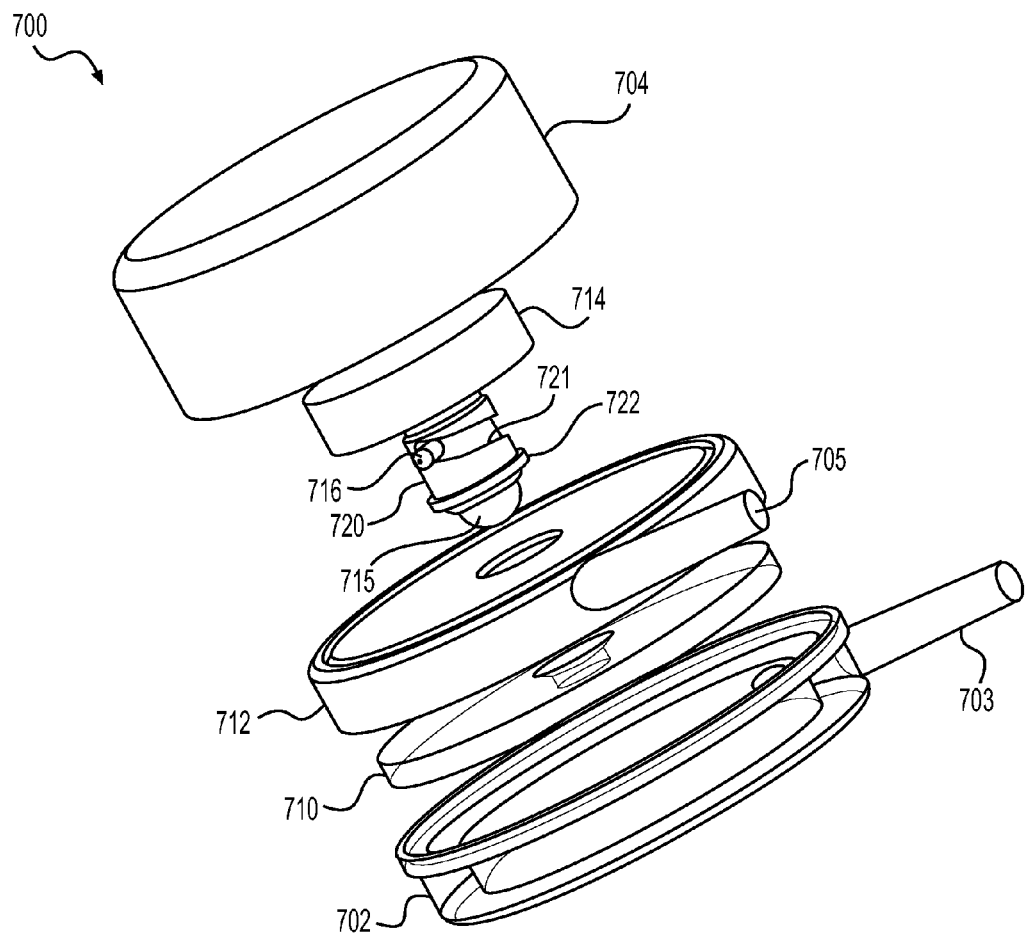
FIGS. 7A and 7B show exemplary devices, in accordance with one or more embodiments of the present disclosure.
Figure 7B:
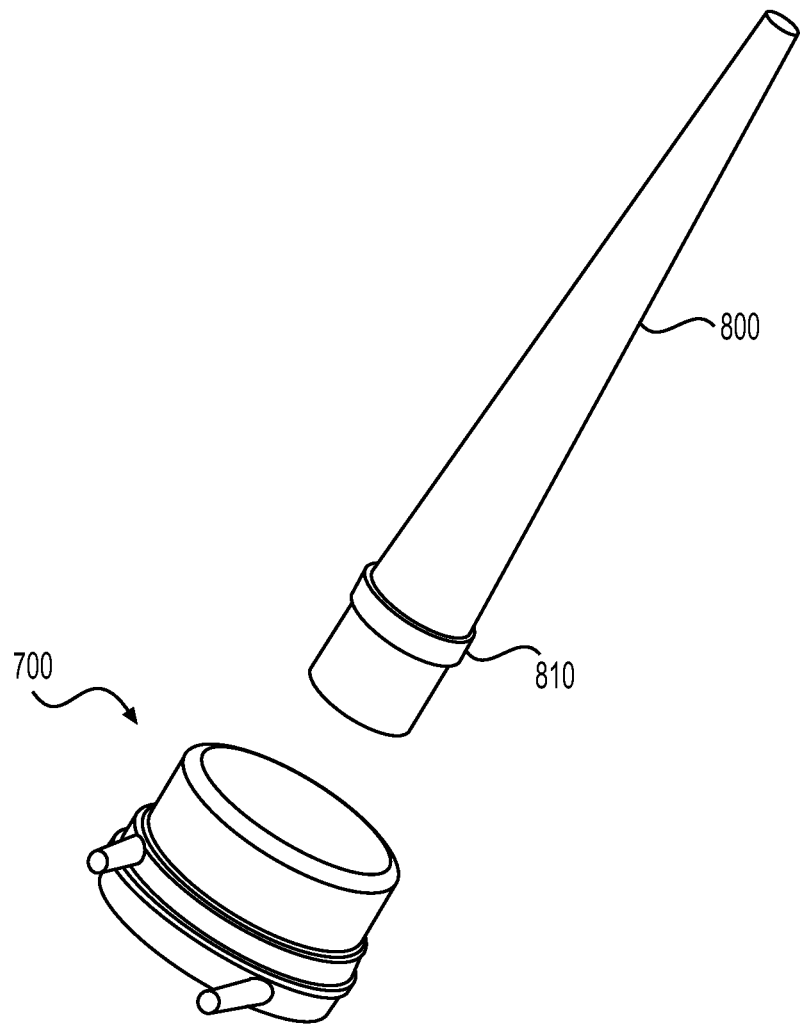

FIG. 7A shows an exploded view of another exemplary valve 700 (e.g., first component) for implantation within the body according to some aspects of the present disclosure. FIG. 7B shows an assembled view of the valve 700 and an exemplary control device 800 (e.g., second component) for controlling the valve 700. As shown in FIG. 7A, the valve 700 may include a lower housing 702, a valve seat 710, a partition 712, a sealing element 715, a sleeve 720, a magnet 714, and an upper housing 704.

The lower housing 702 may include a first opening 703, and the partition 712 may include a second opening 705, wherein fluid may enter and exit the valve 700 via the first and second openings 703, 705. For example, the first opening 703 may serve as an inlet and the second opening 705 may serve as an outlet, or vice-versa. The first and second openings 703, 705 may have any orientation relative to each other. For example, while FIGS. 7A and 7B show the openings 703, 705 facing in generally the same direction, in some embodiments the openings 703, 705 may be on opposite sides of the valve 700, e.g., positioned about 180 degrees apart, or may have any other orientation relative to each other. Further, the openings may be located on other portions of the valve 700. For example, the first opening 703 may be located on the bottom surface of the lower housing 702, e.g., such that the openings 703, 705 extend along generally perpendicular planes.

The sealing element 715 may be coupled to a lower surface of the magnet 714 via any suitable connection, such that the magnet 714 and sealing element 715 move together as a unit. For example, rotating the magnet 714 about a central axis likewise may rotate the sealing element 715 together with the magnet 714. The sealing element 715 may extend in a direction toward the lower housing 702, and may be generally cylindrical in shape or have any other suitable shape. The sleeve 720 may surround a portion of the sealing element 715. In some embodiments, the sleeve 720 may be moveable relative to the sealing element 715 and magnet 714.

The valve seat 710 and the partition 712 may include apertures that are at least partially or completely aligned with each other and with the sealing element 715. While FIG. 7A shows the valve seat 710 and partition 712 as being circular in shape and concentric with a central circular aperture, other shapes such as polygonal and other locations for the apertures are possible. In some embodiments, the aperture in the partition 712 may be larger than the aperture in the valve seat 710, such that the sealing element 715 may pass through the aperture in the partition 712 to contact the valve seat 710. For example, the sealing element 715 may have a rounded, ball-like tip configured to form a seal with the valve seat 710 by blocking the aperture in the valve seat 710. As fluid enters the valve 700 through the first opening 703, for example, the sealing element 715 may be used to selectively control the flow of fluid through the aperture in the partition 712 to exit via the second opening 705. Similarly, fluid may enter the valve 700 through the second opening 705, and the sealing element 715 may selectively control the flow of fluid through the partition 712 to exit the valve 700 via the first opening 703.

In some embodiments, the sleeve 720 may be moveable relative to the sealing element 715 and the magnet 714, but fixed relative to the partition 712. For example, the sleeve 720 may include a lower flange 722 fixed to a lower surface of the partition 712 (e.g., a surface of the partition 712 that faces the valve seat 710). Thus, for example, the magnet 714 and sealing element 715 may move relative to the sleeve 720 and partition 712.

In some embodiments, the sealing element 715 may include a protrusion 716 extending radially outward, and the sleeve 720 may include a spiral slot 721 to receive the protrusion 716. Rotating the magnet 714 and the sealing element 715 may cause the protrusion 716 to move within the slot 721, in turn driving axial movement of the magnet 714 and the sealing element 715 relative to the partition 712. For example, rotating the magnet 714 as shown in FIG. 7A counterclockwise likewise may rotate the sealing element 715 counterclockwise to drive the sealing element 715 to move axially through the partition 712, towards the lower housing 702, as the protrusion 716 moves counterclockwise through the slot 721. Similarly, rotating the magnet 714 clockwise may drive the sealing element 715 to move axially through the partition 712, towards the upper housing 704, as the protrusion 716 moves clockwise through the slot 721.

Each of the lower housing 702, valve seat 710, partition 712, sealing element 715, sleeve 720, and upper housing 704 may comprise any biocompatible material such as, e.g., one or more polymers (including plastics), metals, metal alloys, ceramics, minerals, or any combination thereof. In some embodiments, the valve seat 710 may comprise a rigid plastic, e.g., a polymer that is fat resistant to prevent absorption of lipid-rich fluid passing through the valve 700. The magnet 714 may comprise iron or other suitable magnetic material, such as nickel, cobalt, combinations thereof, or alloys thereof.

The magnet 714 may be rotated via any suitable mechanism in order to control fluid flow through the valve 700 by moving the sealing element 715 towards and away from the valve seat 710. For example, another magnet outside the valve 700 may be aligned with the magnet 714 inside the valve 700 and rotated clockwise or counterclockwise to cause a corresponding rotation of the magnet 714. The components of the valve 700 (e.g., the length of the slot 721) may be configured to provide a predetermined angle of rotation to open or close the valve 700. In some embodiments, for example, a rotation of about 120 degrees may cause the valve 700 to open or close completely, with smaller angles of rotation partially opening or closing the valve 700 as the sealing element 715 forms a partial seal against the sealing element 710. In some embodiments, a rotation greater than 120 degrees, e.g., about 180 degrees, about 270 degrees, about 360 degrees, or more than 360 degrees may cause the valve 700 to open or close completely. In some embodiments, a rotation less than 120 degrees, e.g., about 90 degrees, about 45 degrees, or less than 45 degrees, may cause the valve 700 to open or close completely.

FIG. 7B shows an exemplary control device 800 that includes a magnet 810 for controlling the magnet 714 inside the valve 700. As shown, the control device 800 has an elongated, rod-like shape with the magnet 810 positioned close to one of the ends of the control device 800. Thus, for example, the control device 800 may be brought in close proximity of the valve 700 (e.g., resting on or near an external surface of the body), generally aligned with the magnet 714 inside the valve 700, and rotated to open or close the valve 700 as discussed above. The magnet 810 may be spaced a short distance from the end of the control device 800 to reduce the attractive force between the magnets 714, 810 when the control device 800 is in close proximity to the valve 700, while ensuring that the attractive force is sufficient to cause the magnet 714 to rotate. Other suitable devices comprising a magnet may be used to control the valve 700 manually.

In addition, or as an alternative to manual control, the valve 700 may be controlled electronically. For example, an electronic device such as controller module 500 discussed above may be used to open and close the valve 700 according to a predetermined set of parameters, physiological conditions or stimuli detected within the body (e.g., via sensors implanted in the body and in communication with the controller module 500), and/or via user input received by the controller module 500. Referring to FIG. 5A, for example, the power source 508 may be configured to rotate the coil 510 and/or core element 512 in addition to turning the magnetic field on and off, e.g., based on information received from the integrated circuit 506 as discussed above. Thus, for example, the controller module 500 may be used to rotate the magnet 714 by a specific angle at a particular time of day, instructing the valve 700 to open and close at prescribed times preceding, during, and/or following ingestion of food or drink.

Redirecting a fluid according to the methods presently disclosed may be continuous, intermittent, or one or more periods of continuous flow combined with one or more periods of intermittent flow. The shunting device may include one or more control mechanisms configured to allow for on/off control of a fluid flow. The control mechanism(s) may include, for example, a sensor to detect the amount of fluid present and/or absence, presence, or concentration of a particular compound or combination of compounds in the fluid, and means for increasing, decreasing, initiating, and/or terminating flow through the shunting device. In some embodiments, the control mechanism may temporarily block fluid communication through the shunting device.

Surgical Intervention

The shunting device may be implanted percutaneously, endoscopically, laparoscopically, or open abdomen. In some embodiments, the shunting device may be implanted non-invasively. The shunting device may be configured for short-term or long-term implantation. In at least some embodiments of the present disclosure, implantation of the shunting device may be reversible, i.e., the shunting device can be removed. A control mechanism such as the valve 400 may be coupled to the shunting device prior to implantation.

In one embodiment, for example, the shunting device may be introduced through a catheter via the left subclavian vein and advanced through the thoracic duct to reach the CC. The shunting device may be introduced via other veins and advanced through the body to reach the CC, depending on the location of the CC within a particular patient. An incision or puncture may made in the wall of the CC, allowing the distal end of the shunting device (e.g., a side port extending from the proximal end of the shunting device as shown in FIGS. 2A-2C) to extend outside the CC while the proximal end of the shunting device remains inside the CC. For example, the wall of the CC may be punctured via a needle, wire, bullet tip wire, or other puncturing device. A guide tract may then extend from the side port of the shunting device to enter the ureter, e.g., right ureter or left ureter. The shunting device subsequently may be anchored to tissue at the proximal and/or distal end with an anchoring mechanism to create the fistula. Other percutaneous methods of delivery may also be contemplated, such as implantation through a femoral vein or an internal jugular vein.

The shunting device may also be implanted via retrograde delivery through the bladder. In such embodiments, the shunting device may be introduced through a catheter via the urethra through the bladder. Depending on whether the fistula is established between the bladder, ureter, or kidney (e.g., the calyx or renal pelvis), the shunting device may be further advanced in order to create the fistula. For example, in some embodiments, the shunting device may be implanted endoscopically by passing through the bladder into the right ureter, or may be implanted cytoscopically. The ureter wall may be pierced and the tissues anastomosed to the CC. This approach may leave the distal end of the shunting device in the ureter or the bladder for potential removal later.

In other embodiments, the shunting device may be implanted laparscopically or via open abdomen with or without radiographic guidance. For example, a passageway may be established from the body surface to the CC and the shunting device secured via a circular mesh region at each end that can be fixed to the tissue with an adhesive, a fibrin sealant, a hydrogel material, or extension tines, or may also be stapled to the tissue. In some embodiments, the shunting device may include flexible inner coils or coaxial coils coated with a GORE™ PTFE coating. Additional methods of implantation suitable for the present disclosure will be known to those of ordinary skill in the art. For example, the CC may be accessed via a posterior approach, e.g., lateral to the spine.

Suitable imaging may be used to assist in placement of the device. For example, the shunting device may include a material, e.g., radiopaque material, that is visible by fluoroscopy to assist in implanting the device in a desired location. Further, digital radiographs may assist in post-operative placement, maintenance, and/or monitoring of the device.

Supplemental Treatment

Elimination of fat in the urine may be painful, for example causing hypoproteinemia, edema, nausea, vomiting, diarrhea, abdominal pain, and/or backaches. Lymph fluid comprises white cells, electrolytes, albumin, globulins and fibrinogen, for example, such that loss of chyle in the urine may lead to a loss of these materials. A patient may also develop a clot. In some cases, for example, chyle may form a clot, potentially leading to renal colic or bladder colic. Accordingly, some embodiments of the present disclosure include lifestyle changes such as changes in diet and/or fluid intake. In some embodiments, a patient may be prescribed a treatment regime following implantation of the device. For example, a physician or other healthcare provider may prescribe medication, such as an analgesic, to alleviate pain. Other medications may be prescribed to facilitate or otherwise assist in breaking down lipids in the urine, or to facilitate or increase flow (e.g., use of a diuretic such as furosemide). The patient may be advised how to dilute the urine to alleviate potential pain, such as ingesting fluids to break down and/or dilute lipids before excretion in the urine in order to avoid pain. Alternatively or in addition, the patient may be advised to follow a low-fat and/or high-protein diet. A high-protein diet may help to compensate for a loss of protein, e.g., due to hypoproteinemia and/or following the formation of a clot. Loss of lymph fluid may impact other health parameters of a patient, such as the patient's immune system. Treatment regimes according to the present disclosure may include monitoring one or more health parameters of the patient, such as immunoglobulin levels and/or T cell levels.

Other embodiments of the present disclosure will be apparent to those skilled in the art from consideration of the specification and practice of the embodiments disclosed herein. It is intended that the specification and examples be considered as exemplary only, with a true scope and spirit of the present disclosure being indicated by the following claims.

We claim:

1. A medical device for redirecting at least a portion of a fluid in a patient, the medical device comprising:
   a housing having an inlet and an outlet for passage of the fluid through the housing, the housing including:
   a diaphragm;
   at least one metallic element coupled to the diaphragm, the at least one metallic element comprising a ferrous material, wherein the diaphragm and the at least one metallic element define a conduit for passage of the fluid therethrough; and
   a sealing element at least partially aligned with the conduit to selectively block passage of the fluid; and
   a controller including an electromagnet and an integrated circuit;
   wherein the controller is configured to selectively allow and prevent passage of the fluid through the conduit by magnetic attraction to the at least one metallic element, wherein the medical device is configured to redirect at least a portion of a fluid from a thoracic duct, the fluid including lipids.

2. The medical device of claim 1, wherein the diaphragm includes a flexible material and is configured to move in a direction towards and away from the sealing element.

3. The medical device of claim 1, wherein the housing includes an upper housing including the inlet and a lower housing including the outlet.

4. The medical device of claim 3, wherein the sealing element is coupled to the lower housing, a position of the sealing element being adjustable relative to the lower housing.

5. The medical device of claim 1, wherein the electromagnet includes a coil and a power source.

6. The medical device of claim 5, wherein the electromagnet further includes a core element disposed within the coil, the core element comprising a ferrous material.

7. The medical device of claim 1, wherein the integrated circuit is configured to supply and terminate power to the electromagnet for controlling a magnetic field generated by the electromagnet.

8. The medical device of claim 7, wherein the integrated circuit is in communication with at least one sensor.

9. The medical device of claim 8, wherein the at least one sensor is configured to measure physiological information about the patient, and the integrated circuit is configured to control the magnetic field based at least in part on the physiological information.

10. The medical device of claim 9, wherein the physiological information includes at least one of a presence of the fluid, an absence of the fluid, a flow rate of the fluid, a pressure, or a temperature.

11. The medical device of claim 7, wherein the integrated circuit is configured to control the magnetic field to allow passage of the fluid at one or more timed intervals.

12. The medical device of claim 7, wherein the controller includes an actuator, and the integrated circuit is configured to control the magnetic field in response to the actuator.

13. A medical device for redirecting at least a portion of a fluid in a patient, the medical device comprising:
   a housing having an inlet and an outlet for passage of the fluid through the housing, the housing including:
   a diaphragm;
   at least one metallic element coupled to the diaphragm, the at least one metallic element comprising a ferrous material, wherein the diaphragm and the at least one metallic element define a conduit for passage of the fluid therethrough; and a sealing element at least partially aligned with the conduit to selectively block passage of the fluid; and a controller including an electromagnet and an integrated circuit, wherein the integrated circuit is configured to supply and terminate power to the electromagnet for controlling a magnetic field generated by the electromagnet, and the integrated circuit is configured to control the magnetic field to allow passage of the fluid at one or more timed intervals;

wherein the controller is configured to selectively allow and prevent passage of the fluid through the conduit by magnetic attraction to the at least one metallic element, wherein the one or more timed intervals relates to an ingestion of food or drink.

14. A method of treating a patient, comprising:

generating a magnetic field between an electromagnet and a medical device implanted in the patient, the medical device including:

an inlet and an outlet for passage of a fluid through the medical device;

a diaphragm;

at least one metallic element coupled to the diaphragm, wherein the diaphragm and the at least one metallic element define a conduit; and a sealing element at least partially aligned with the conduit;

wherein the magnetic field controls passage of the fluid through the medical device, and the fluid includes a fluid from a thoracic duct of the patient.

* * * * *